United States Patent [19]
Sanghvi et al.

[11] Patent Number: 5,969,118
[45] Date of Patent: Oct. 19, 1999

[54] BACKBONE MODIFIED OLIGONUCLEOTIDE ANALOGS AND PREPARATION THEREOF THROUGH RADICAL COUPLING

[75] Inventors: Yogesh S. Sanghvi; Phillip Dan Cook, both of Carlsbad, Calif.

[73] Assignee: Isis Pharmaceuticals, Inc., Carlsbad, Calif.

[21] Appl. No.: 08/794,493

[22] Filed: Feb. 4, 1997

Related U.S. Application Data

[62] Division of application No. 08/300,072, Sep. 2, 1994, Pat. No. 5,618,704, which is a continuation of application No. 08/040,933, Mar. 31, 1993, abandoned, which is a continuation-in-part of application No. PCT/US92/04294, May 21, 1992, abandoned, and a continuation-in-part of application No. 07/903,160, Jun. 24, 1992, abandoned, which is a continuation-in-part of application No. 07/703,619, May 21, 1991, Pat. No. 5,378,825, which is a continuation-in-part of application No. 07/566,836, Aug. 13, 1990, Pat. No. 5,223,618, and a continuation-in-part of application No. 07/558,663, Jul. 27, 1990, Pat. No. 5,138,045.

[51] Int. Cl.$^6$ .......................... C07H 19/00; C07H 21/02; C07H 19/06; C07H 21/00
[52] U.S. Cl. ................... 536/22.1; 536/23.1; 536/28.54; 536/25.3
[58] Field of Search ................................ 536/22.1, 23.1, 536/28.54, 25.3

[56] References Cited

U.S. PATENT DOCUMENTS

| | | | |
|---|---|---|---|
| 3,687,808 | 8/1972 | Merigan, Jr. et al. | 195/28 |
| 4,997,924 | 3/1991 | Jarvi et al. | 536/26 |
| 5,174,962 | 12/1992 | Brennan | 422/78 |
| 5,235,033 | 8/1993 | Summerton et al. | 528/391 |
| 5,378,825 | 1/1995 | Sanghvi et al. | 536/25.34 |

FOREIGN PATENT DOCUMENTS

| | | |
|---|---|---|
| 0287313 | 10/1988 | European Pat. Off. . |
| 0381335 | 1/1990 | European Pat. Off. . |
| 0378518 | 7/1990 | European Pat. Off. . |
| 0417999 | 3/1991 | European Pat. Off. . |
| WO 86/05518 | 9/1986 | WIPO . |
| WO 90/08156 | 7/1990 | WIPO . |
| WO 92/02534 | 2/1992 | WIPO . |
| WO 92/03568 | 3/1992 | WIPO . |
| WO 92/05186 | 4/1992 | WIPO . |
| WO93/18052 | 9/1993 | WIPO . |

OTHER PUBLICATIONS

Abdel-Magid et al., "Reductive Amination of Aldehydes and Ketones by Using Sodium Triacetoxyborohydride,".
Egholm et al., Peptide Nucleic Acids (PNA). Oligonucleotide Analogues with an Achiral Peptide.
Giannis et al., "Fragmentation and Wittig Olefination of Glucosamine Derivatives—A Simple Route to Open Chain Amino Sugars and Chiral Glyerols," *Tetrahedron*, 44:7177–7180, 1988.
Goodchild, Conjugates of Oligonucleotides and Modified Oligonucleotides: A Review of Their Synthesis and.
Greene et al., *Protective Groups in Organic Synthesis*, John Wiley & Sons, Inc., 1991, pp. 175–223.
Horwitz et al., "Nucleotides. V. The Nonomesylates of 1–(2'–Deoxy–β–D–lynofuranosyl) thymine," *J. Org. Chem.*, 29:2076, 1964.
Hyrup et al., "Modification of the Binding Affinity of Peptide Nucleic Acids (PNA). PNA with Extended Backbones consisting of 2–Aminoethyl–β–alanine or 3–Aminopropylglycine Units," *J. Chem. Soc. Chem. Comm.*
Inouye et al., "Selective Coloration of Spiro Pyridopyrans for Guanosine Derivatives," J. Am. Chem.
Jenkins et al., "9–(2–Methyl–β–D–ribofuranosyl) adenine (2'–Methyladenosine," *Synthetic Procedures in Nucleic*.
Lin et al., "Synthesis and Biological Activity of Several Amino Analogues of Thymidine," *J. Med. Chem.*, 21:109–112, 1978.
Ma et al., "Design and synthesis of RNA miniduplexes via a synthetic linker approach. 2. Generation of covalently closed, double–stranded cyclic HIV–1 TAR RNA analogs with high Tat–binding affinity," *Nucleic*.
Matsuda et al., Synthesis and Biological Activities of 3'–Deoxy–3'–Isocyano,–Isothiocyano, and –Isoselenocyano–.
Nair et al., "Regiospecific 5'–Silylation of Nucleosides," *Org. Prep. Procedures Int.*, 22:57–61, 1990.
Pauling, "Molecular Architecture and Biological Reactions," *Chem. Eng. News*, 24:1375–1377, 1946.
Perkins et al., "Accelerated Displacement of Duplex DNA Strands by a Synthetic Circular Oligodeoxynucleotide,".
Poopeiko et al., "A Simple Method for Azido Group Reduction," *Syn. Lett.*, 342, 1991.
Prakash et al., Molecular Recognition by Circular Oligonucleotides. Strong Binding of Single–stranded DNA.
Rebek, Jr., "Molecular Recognition and Biophysical Organic Chemistry," *Ace. Chem. Res.*, 23:399–404, 1990.
Rentzeperis et al., Contribution of Loops and Nicks to the Formation of DNA Dumbbells: Melting Behavior and.
Sanghvi et al., "Synthesis and Structure of Methylene(dimethylhydrazo) Linked Thymidine Dimer and Their Utility as Antisense Oligonucleotides," *Collect. Czech. Chem. Commun.*, 58:158–162, 1993.
Secrist et al., Abstract 21, "Synthesis and Biological Activity of 4'–Thionucleosides," *Program & Abstracts, Tenth International Roundtable, Nucleosides, Nucleotides and their Biological Applications*, Park City.
Sproat et al., "2'–O–Methyloligoribonucleotides: Synthesis and Applications," *Oligonucleotides and Analogs A Practical Approach*, F. Eckstein Ed., IRL Press, p. 55, 1991.

(List continued on next page.)

*Primary Examiner*—Ardin H. Marschel
*Assistant Examiner*—Jezia Riley
*Attorney, Agent, or Firm*—Woodcock Washburn Kurtz Mackiewicz & Norris, LLP

[57] ABSTRACT

Methods for preparing oligonucleotide analogs which have improved nuclease resistance and improved cellular uptake are provided. In preferred embodiments, the methods involve radical coupling of 3'- and 5'-substituted or 5'- and 3'-subutituted nucleosidic synthons.

12 Claims, No Drawings

OTHER PUBLICATIONS

Trapani et al., "N–1–Alkenyl–N, S–Diacyl–2–Aminobenzenethiols (Enamides) by Ring-Opening of 2,3–Dihydro–1,3–benzothiazoles with Aliphatic Carboxylic Anhydrides," *Synthesis*, 84, 1988.

Trost et al., ed., *Comprehensive Organic Synthesis*, vol. 4, pp. 758–776, 1991.

Tuladhar et al., "A Synthetic Route to Poly–N, N'–Dimethylethylenediamines," *Tet. Letts.*, 33:2203–2206, 1992.

Yamamoto et al., "One–Step Synthesis of 5'–Azido–nucleosides," *J. Chem. Soc. Perkin I*, 306–310, 1980.

Zuckermann et al., "Efficient Method for the Preparation of Peptoids [Oligo(N–substituted glycines)] by Submonomer Solid–phase Synthesis," *J. Am. Chem. Soc.*, 114:10646–10647, 1992.

Puglisi et al., "Absorbance Melting Curves of RNA," *Methods in Enzymology*, 180:304–325, 1989.

Kool et al. J. Chem. Soc. Chem. Commun. 1991 1161.

Morr et al. Building Blocks for the Chemical Synthesis of DNA Containing C(3')–CH2–P Bonds in Chemical Synthesis in Nolecular Biology GBF (Gesellschaft fueunsch Biotecnolgiesche Forschung Branweig–Stoeckheim) Bloecker et al. eds. 987 8:107–113.

Grant et al. Hackh's Chemical Dictionary 4th. Ed. McGraw–Hill NY 1969 pp. 27,466,569, and 575.

MacCoss et al. "A new synthetic use of nucleoside N–oxides" J. Org. Chem., vol. 45, pp. 788–794, 1980.

Griengl et al. "5–(Haloalkyl)–2'–deoxyuridines: A novel type of potent antiviral nucleoside analogue" J. Med. Chem. vol. 28, pp. 1679–1684, 1985.

Cushley et al. "Nucleosides. XLIX. Nuclear magnetic resonance studies of 2'– and 3'–halogeno nucleosides. The conformations of 2'–deoxy–2'fluorouridine and 3'–deoxy–3'–fluoro– –D–arabinofuranosyluracyl" Canadian Journal of Chemistry, vol. 46, pp. 1131–1111, 1968.

Bankston et al., "A Short Synthesis of 5'–O–Trityl–Protected threo– and erythro– 3'–Cyano–3'–doexythymidine Epimers Using Free–Radical Chemistry," *J. Het. Chem.*, 29:1405–1407, 1992.

Barton et al., "A "One–Pot" Synthesis of Sulfenamides," *J. Org. Chem.*, 56:6702–6704,, 1991.

Barton et al., "Stereoselectivity in Radical Reactions of 2'–Deoxynucleosides. A Synthesis of an Isostere of 3'–Azido–3'–Deoxythymidine–5'–Monophosphate," *Tetrahedron Letters*, 30:4969–4972, 1989.

Baud et al, "Improved Procedure for the Regiospecific Synthesis of 2'–Deoxyribonucleosides," *Tetrahedron Letters*, 31:4437–4440, 1990.

Beaucage et al., "Advances in the Synthesis of Oligonucleotides by the Phosphoramidite Approach," *Tetrahedron*, 48:2223–2311, 1992.

Bodenteich et al., "Synthesis of Enantiomerically Pure Carbocyclic 3'–Azido–2',3'–Dideoxythymidine, A Potential Anti–Aids Drug," *Tetrahedron Letters*, 28:5311–5312, 1987.

Camarasa et al., "Aldol Reaction of Nucleoside 5'–Carboxaldehydes with Acetone, Synthesis of 5'–C–Chain Extended Thymidine Derivatives," *Nucleosides and Nucleotides*, 9:533–546, 1990.

Cormier et al., "Synthesis of hexanucleotide analogues containing diisopropylsilyl internucleotide linkages," *Nucleic Acids Research*, 16:4583–4594, 1988.

Cosstick et al., "Synthesis and properties of dithymidine phosphate analogues containing 3'–thiothymidine," *Nucleic Acids Res.*, 18:829–835, 1990.

Debart et al., "Intermolecular Radical C—C Bond Formation: Synthesis of a Novel Dinucleoside Linker for Non–anionic Antisense Oligonucleotides," *Tet. Lett.*, 33:2645–2648, 1992.

Etzold et al., "The Extension of the Sugar Chain of Thymidine: a New Route to 5'–Deoxyhexose Nucleosides," *J.C.S. Chem. Comm.*, 422, 1968.

Fiandor et al., "Synthesis of 3'–deoxy–3'–(2–propynyl)thymidine and 3'–cyanamethyl–3'–deoxythymidine, analogs of AZT," *Tet. Lett.*, 31:597–600, 1990.

Fikes et al., "Preassociating α–Nucleophiles," *J. Am. Chem. Soc.*, 114:1493–1496, 1992.

Fleet et al., "Methyl 5–O–Tert–Butyldiphenylsilyl–2–αβ–D–Threo–Pentofuranoside as a Divergent Intermediate for the Synthesis of 3'–Substituted–2',3'–Dideoxynucleosides: Synthesis of 3'–Azido–3'–Deoxythymidine, 3'–Deoxy–3'–Fluorothymidine and 3'–Cyano–3'–Deoxythymidine," *Tetrahedron*, 44:625–636, 1988.

Gait, M.J., ed., *Oligonucleotide Synthesis, A Practical Approach*. Washington, D.C.: IRL Press, 1984, Chapter 3, pp. 35–81.

Hanamoto et al., "SmI$_2$–Promoted Ketyl Radical Addition to O–Benzyl Formaldoxime. A New Aminomethylation," *Tet. Letts.* 32:3555–3556, 1991.

Hart et al., "Bis(trimethylstannyl) benzopinacolate–Mediated Intermolecular Free–Radical Carbon—Carbon Bond–Forming Reactions: A New One–Carbon Homologation," *J. Am. Chem. Soc.*, 110:1631–1633, 1988.

Hillgartner et al., "Bix(trimethylzinn)benzpinakolat, seine reversible radikalische Dissoziation und Reaktionen," *Liebigs. Ann. Chem.*, 586–599, 1975.

Hronowski et al., "Synthesis of New Carbocyclic Analogues of 3'–Azido– and 3'–Amino–2',3'–dideoxynucleosides," *J. Chem. Soc., Chem. Commun.*, 1547–1548, 1990.

Jones et al., "The Synthesis of 6'–Deoxyhomonucleoside–6'–phosphonic Acids," *J. Amer. Chem. Soc.*, 90:5337–5338, 1968.

Jones et al., "Synthesis of Carbocyclic Nucleosides: Preparation of (−)–5'–Homoaristeromycin and Analogues," *J. Chem. Soc. Perkin Trans. I*, 2927–2932, 1988.

Koster et al., "Diakyl aluminum chloride: A reagent for removal of trityl group from trityl ethers of deoxynucleosides, deoxynucleotides, and oligodeoxynucleotides," *Tet. Letts.* 23:26421–2644, 1982.

Loke et al., "Delivery of c–myc Antisense Phosphorothioate Oligodeoxynucleotides to Hematopoietic Cells in Culture by Liposome fusion: Specific Reduction in c–myc Protein Expression Correlates with Inhibition of Cell Growth and DNA Synthesis," *Top. Microbiol. Immunol.*, 141:282–289, 1988.

Marcus–Sekura et al., "Comparative inhibition of chloramphenicol acetyltransferase gene expression by antisense oligonucleotide analogues having alkyl phosphotriester, methylphosphonate and phosphorothioate linkages," *Nuc. Acids Res.* 15:5749–5763, 1987.

Matteucci, "Deoxyoligonucleotide Analogs Based on Formacetal Linkages," *Tetrahedron Letters*, 31:2385–2388, 1990.

Mazur et al., "Isosteres of Natural Phosphates. 11. Synthesis of a Phosphonic Acid Analogue of an Oligonucleotide," *Tetrahedron*, 40:3949–3956, 1984.

Miller et al., "Effects of a Trinucleotide Ethyl Phosphotriester, G'''p (Et) G'''p (Et)U, on Mammalian Cells in Culture," *Biochemistry*, 16:1988–1996, 1977.

Motawia et al., "A New Route to 2',3'-Dideoxycytidine," *Liebigs Ann. Chem.*, 599–602, 1990.

Nicolaou et al., "Carbocyclic Thromboxane $A_2$," *J. Am. Chem. Soc.*, 102:1404–1409, 1980.

Nielsen et al., "Sequence–Selective Recognition of DNA by Strand Displacement with a Thymine–Substituted Polyamide," *Science*, 254:1497–1500, 1991.

Niitsu et al., "Synthesis of a Series of Linear Pentaamines with Three and Four Methylene Chain Intervals," *Chem. Pharm. Bull.*, 34:1032–1038, 1986.

Parkes et al., "A Short Synthesis of 3'-Cyano-3'-Deoxythymidine," *Tetrahedron Letters*, 29:2995–2996, 1988.

Rawson et al., "The Synthesis of 5'-Homo-2'-Deoxycytidine," *Nucleosides & Nucleotides*, 9:89–96, 1990.

Shaw et al., "Modified deoxyoligonucleotides stable to exonuclease degradation in serum," *Nucleic Acids Research*, 19:747–749, 1991.

Stirchak et al., "Uncharged Stereoregular Nucleic Acid Analogues. 1. Synthesis of a Cytosine–Containing Oligomer with Carbamate Internucleoside Linkages," *Journal of Org. Chem.*, 52:4202–4206, 1987.

Vasseur et al., "Oligonucleotides: Synthesis of a Novel Methylhydroxylamine–Linked Nucleoside Dimer and Its Incorporation into Antisense Sequences," *J. Am. Chem. Soc.*, 114:4006–4007, 1992.

Verheyden et al., "Halo Sugar Nucleosides. I. Iodination of Primary Hydroxyl Groups of Nucleosides with Methyltriphenoxyphosphonium Iodide," *J. Org. Chem.*, 35:2319–2326, 1970.

Verheyden et al., "Halo Sugar Nucleosides. II. Iodination of Secondary Hydroxyl Groups of Nucleosides with Methyltriphenoxyphosphonium Iodide," *J. Org. Chem.*, 35:2868–2877, 1970.

Wilson, D.B., "Cellular Transport Mechanisms," *Ann. Rev. Biochem.*, 47:933–965, 1978.

Wu et al., "New Synthesis of 2',3–Dideoxy–3'–C–Cyano–2'–Substituted Thymidines by Michael Addition Reactions," *Tetrahedron*, 855–862, 1989.

Yang et al., "Construction of Glycosidic N—O Linkages in Oligosaccharides," *J. Am. Chem. Soc.*, 113:4715–4716, 1991.

Halford & Jones, "Synthetic Analogues of Polynucleotides," *Nature*, 217, (1968), 638–639.

Magid et al. Reductive Amination of Aldehydes and ketones by Using Sodium Triacetoxyborohydride, Tetrahedron Letters 1990 31:5595.

Heinemann et al. Effect of a Single 3'–methylene Phophonate Linkage on the Conformation of an A–DNA Octamer Double Helix,Nucleic Acids Res. 1991 19(3) :427–.

Neumeyer et al. J. Org. Chem. 1973 38:2291.

Alinger et al. Organic Chemistry Worth Publ. NY 1971 388–389.

SEQUENCE LISTING (1) GENERAL INFORMATION:

(iii) NUMBER OF SEQUENCES: 1

(2) INFORMATION FOR SEQ ID NO: 1:

(i) SEQUENCE CHARACTERISTICS:
      (A) LENGTH: 11
      (B) TYPE: nucleic acid
      (C) STRANDEDNESS: single
      (D) TOPOLOGY: linear (iv) ANTI-SENSE: No (xi) SEQUENCE DESCRIPTION: SEQ ID NO: 1:

TTTTTTTTTT C                                        11

BACKBONE MODIFIED OLIGONUCLEOTIDE ANALOGS AND PREPARATION THEREOF THROUGH RADICAL COUPLING

CROSS REFERENCE TO RELATED APPLICATIONS

This patent application is division of patent application Ser. No. 08/300,072, filed on Sep. 2, 1994 (now U.S. Pat. No. 5,618,704), which is a continuation of patent application Ser. No. 08/040,933, filed on Mar. 31, 1993 (now abandoned). Ser. No. 08/040,933 is a continuation-in-part of application Ser. No. 07/903,160, filed on Jun. 24, 1992 (now abandoned), and application PCT/US92/04294, filed on May 21, 1992 (now abandoned). Application Ser. No. 07/903,160 is a continuation-in-part of application Ser. No. 07/703,619, filed on May 21, 1991 (now U.S. Pat. No. 5,378,825), application Ser. No. 07/566,836, filed on Aug. 13, 1990 (now U.S. Pat. No. 5,223,618), application Ser. No. 07/558,663, filed on Jul. 27, 1990 (now U.S. Pat. No. 5,138,045), and application PCT/US92/04294. Application PCT/US92/04294 is a continuation-in-part of application Ser. No. 07/703,619, which is a continuation-in-part of application Ser. No. 07/566,836 and application Ser. No. 07/558,663. This patent application also is related to the subject matter disclosed and claimed in application Ser. No. 08/039,979, filed on Mar. 30, 1993 (now abandoned), application Ser. No. 08/039,846, filed on Mar. 30, 1993 (now abandoned), application Ser. No. 08/040,526, filed on Mar. 31, 1993 (now U.S. Pat. No. 5,489,677), and application Ser. No. 08/040,903, filed on Mar. 31, 1993 (now U.S. Pat. No. 5,386,023). Each of these patent applications are assigned to the assignee of this patent application and are incorporated by reference herein.

FIELD OF THE INVENTION

This invention relates to the design, synthesis and application of nuclease resistant oligonucleotide analogs which are useful for therapeutics, diagnostics and as research reagents. Oligonucleotide analogs are provided having modified linkages replacing the phosphorodiester bonds that serve as inter-sugar linkages in wild type nucleic acids. Such analogs are resistant to nuclease degradation and are capable of modulating the activity of DNA and RNA. Methods for synthesizing these oligonucleotide analogs and for modulating the production of proteins also are provided.

BACKGROUND OF THE INVENTION

It is well known that most of the bodily states in mammals, including most disease states, are effected by proteins. Proteins, either acting directly or through their enzymatic functions, contribute in major proportion to many diseases in animals and man.

Classical therapeutics generally has focused upon interactions with proteins in an effort to moderate their disease causing or disease potentiating functions. Recently, however, attempts have been made to moderate the production of proteins by interactions with the molecules (i.e., intracellular RNA) that direct their synthesis. These interactions have involved hybridization of complementary "antisense" oligonucleotides or certain analogs thereof to RNA. Hybridization is the sequence-specific hydrogen bonding of oligonucleotides or oligonucleotide analogs to RNA or to single stranded DNA. By interfering with the production of proteins, it has been hoped to effect therapeutic results with maximum effect and minimal side effects.

The pharmacological activity of antisense oligonucleotides and oligonucleotide analogs, like other therapeutics, depends on a number of factors that influence the effective concentration of these agents at specific intracellular targets. One important factor for oligonucleotides is the stability of the species in the presence of nucleases. It is unlikely that unmodified oligonucleotides will be useful therapeutic agents because they are rapidly degraded by nucleases. Modification of oligonucleotides to render them resistant to nucleases therefore is greatly desired.

Modification of oligonucleotides to enhance nuclease resistance generally has taken place on the phosphorus atom of the sugar-phosphate backbone. Phosphorothioates, methyl phosphonates, phosphoramidates and phosphorotriesters have been reported to confer various levels of nuclease resistance. Phosphate-modified oligonucleotides, however, generally have suffered from inferior hybridization properties. See, e.g., Cohen, J. S., ed. *Oligonucleotides: Antisense Inhibitors of Gene Expression*, (CRC Press, Inc., Boca Raton Fla., 1989).

Another key factor is the ability of antisense compounds to traverse the plasma membrane of specific cells involved in the disease process. Cellular membranes consist of lipid-protein bilayers that are freely permeable to small, nonionic, lipophilic compounds and are inherently impermeable to most natural metabolites and therapeutic agents. See, e.g., Wilson, *Ann. Rev. Biochem.* 1978, 47, 933. The biological and antiviral effects of natural and modified oligonucleotides in cultured mammalian cells have been well documented. It appears that these agents can penetrate membranes to reach their intracellular targets. Uptake of antisense compounds into a variety of mammalian cells, including HL-60, Syrian Hamster fibroblast, U937, L929, CV-1 and ATH8 cells has been studied using natural oligonucleotides and certain nuclease resistant analogs, such as alkyl triesters and methyl phosphonates. See, e.g., Miller, et al., *Biochemistry* 1977, 16, 1988; Marcus-Sekura, et al., *Nuc. Acids Res.* 1987, 15, 5749; and Loke, et al., *Top. Microbiol. Immunol.* 1988, 141, 282.

Often, modified oligonucleotides and oligonucleotide analogs are internalized less readily than their natural counterparts. As a result, the activity of many previously available antisense oligonucleotides has not been sufficient for practical therapeutic, research or diagnostic purposes. Two other serious deficiencies of prior art compounds designed for antisense therapeutics are inferior hybridization to intracellular RNA and the lack of a defined chemical or enzyme-mediated event to terminate essential RNA functions.

Modifications to enhance the effectiveness of the antisense oligonucleotides and overcome these problems have taken many forms. These modifications include base ring modifications, sugar moiety modifications and sugar-phosphate backbone modifications. Prior sugar-phosphate backbone modifications, particularly on the phosphorus atom, have effected various levels of resistance to nucleases. However, while the ability of an antisense oligonucleotide to bind to specific DNA or RNA with fidelity is fundamental to antisense methodology, modified phosphorus oligonucleotides have generally suffered from inferior hybridization properties.

Replacement of the phosphorus atom has been an alternative approach in attempting to avoid the problems associated with modification on the pro-chiral phosphate moiety. For example, Matteucci, *Tetrahedron Letters* 1990, 31, 2385 disclosed the replacement of the phosphorus atom with a methylene group. However, this replacement yielded unstable compounds with nonuniform insertion of formacetal linkages throughout their backbones. Cormier, et al., *Nucleic Acids Research* 1988, 16, 4583, disclosed replacement of phosphorus with a diisopropylsilyl moiety to yield homopolymers having poor solubility and hybridization properties. Stirchak, et al., *Journal of organic Chemistry* 1987, 52, 4202 disclosed replacement of phosphorus linkages by short homopolymers containing carbamate or morpholino linkages to yield compounds having poor solubility and hybridization properties. Mazur, et al., *Tetrahedron* 1984, 40, 3949, disclosed replacement of a phosphorus linkage with a phosphonic linkage yielded only a homotrimer molecule. Goodchild, *Bioconjugate Chemistry* 1990, 1, 165, disclosed ester linkages that are enzymatically degraded by esterases and, therefore, are not suitable for antisense applications.

The limitations of available methods for modification of the phosphorus backbone have led to a continuing and long felt need for other modifications which provide resistance to nucleases and satisfactory hybridization properties for antisense oligonucleotide diagnostics and therapeutics.

OBJECTS OF THE INVENTION

It is an object of the invention to provide oligonucleotide analogs for diagnostic, research, and therapeutic use.

It is a further object of the invention to provide oligonucleotide analogs capable of forming duplex or triplex structures with, for example, DNA.

It is a further object to provide oligonucleotide analogs having enhanced cellular uptake.

Another object of the invention is to provide oligonucleotide analogs having greater efficacy than unmodified antisense oligonucleotides.

It is yet another object of the invention to provide methods for synthesis and use of oligonucleotide analogs.

These and other objects will become apparent to persons of ordinary skill in the art from a review of the present specification and the appended claims.

SUMMARY OF THE INVENTION

The present invention provides novel compounds that mimic and/or modulate the activity of wild-type nucleic acids. In general, the compounds contain a selected nucleoside sequence which is specifically hybridizable with a targeted nucleoside sequence of single stranded or double stranded DNA or RNA. At least a portion of the compounds of he invention has structure I:

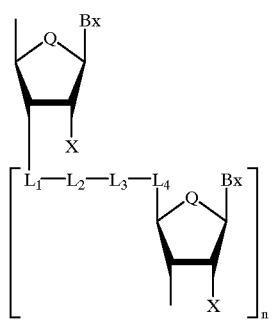

I wherein:

$L_1—L_2—L_3—L_4$ is $CH_2—R_A—NR_1—CH_2$, $CH_2—NR_1—R_A—CH_2$, $R_A—NR_1—CH_2—CH_2$, or $NR_1—R_A—CH_2—CH_2$;

$R_A$ is O or $NR_2$;

$R_1$ and $R_2$ are the same or different and are H; alkyl or substituted alkyl having 1 to about 10 carbon atoms; alkenyl or substituted alkenyl 2 to about 10 carbon atoms; alkynyl or substituted alkynyl having 2 to about 10 carbon atoms; alkaryl, substituted alkaryl, aralkyl, or substituted aralkyl having 7 to about 14 carbon atoms; alicyclic; heterocyclic; a reporter molecule; an RNA cleaving group; a group for improving the pharmacokinetic properties of an oligonucleotide; or a group for improving the pharmacodynamic properties of an oligonucleotide;

$B_X$ is a nucleosidic base;

n is an integer greater than 0;

Q is O, S, $CH_2$, CHF or $CF_2$;

X is H, OH, $C_1$ to $C_{10}$ lower alkyl, substituted lower alkyl, alkaryl or aralkyl, F, Cl, Br, CN, $CF_3$, $OCF_3$, OCN, O-alkyl, S-alkyl, N-alkyl, O-alkenyl, S-alkenyl, N-alkenyl, $SOCH_3$, $SO_2CH_3$, $ONO_2$, $NO_2$, $N_3$, $NH_2$, heterocycloalkyl, heterocycloalkaryl, aminoalkylamino, polyalkylamino or substituted silyl, an RNA cleaving group, a group for improving the pharmacokinetic properties of an ligonucleotide, or a group for improving the pharmacodynamic roperties of an oligonucleotide.

The compounds of the invention generally are prepared by coupling preselected 3'-functionalized and 4'-functionalized nucleosides and/or oligonucleotides under conditions effective to form the above-noted $L_1—L_2—L_3—L_4$ linkages. In preferred embodiments, the linkages are formed by coupling synthons having structures II and III:

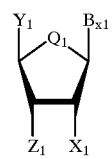

II

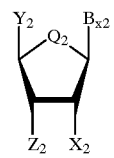

III wherein:

$Z_1$ and $Y_2$ are selected such that:
(i) $Z_1$ is $R_B$ and $Y_2$ is $CH_2—R_A—N=CH_2$; or
(ii) $Z_1$ is $CH_2—R_B$ and $Y_2$ is $R_A—N=CH_2$; or
(iii) $Z_1$ is $CH_2—R_A—N=CH_2$ and $Y_2$ is $R_B$ or
(iv) $Z_1$ is $R_A—N=CH_2$ and $Y_2$ is $CH_2—R_B$;

where the synthon bearing said $R_B$ group being a donor synthon and the synthon bearing said $N=CH_2$ group being an acceptor synthon;

$R_S$ is a radical generating group selected from I, OC(O)O—$C_6H_5$, OC(O)S—$C_6H_5$, Se—$C_6H_5$, O—C(S)O—$C_6F_5$, O—C(S)O—$C_6Cl_5$, O—C(S)O—(2,4,6—$C_6Cl_3$), Br, $NO_2$, Cl, C(S)S-Me, C(S)O—(p-$CH_4F$), bis-dimethylglyoximatopyridine cobalt (i.e., C(dmgH)$_2$PY) OC(S)$C_6H_5$, OC(S)SCH$_3$ OC(S)-imidazole, and C(O)O-pyridin-2-thione;

$Y_1$ and $Z_2$ are, independently, H, hydroxyl, aminomethyl, hydrazinomethyl, hydroxymethyl, C-formyl, phthalimidohydroxy- methyl, aryl-substituted imidazolidino, aminohydroxylmethyl, ortho-methylaminobenzenethio, methylphosphonate, methylalkylphosphonate, a nucleoside, a nucleotide, an oligonucleotide, an oligonucleoside, or a hydroxyl-protected or amine-protected derivative thereof;

$B_{X1}$ and $B_{X2}$ are, independently, nucleosidic bases;

$Q_1$ and $Q_2$ are, independently, O, S, $CH_2$, CHF or $CF_2$; and $X_1$ and $X_2$ are, independently, H, OH, $C_1$ to $C_{10}$ lower alkyl, substituted lower alkyl, alkaryl or aralkyl, F, Cl, Br, CN, $CF_3$, $OCF_3$, OCN, O-alkyl, S-alkyl, N-alkyl, O-alkenyl, S-alkenyl, N-alkenyl, $SOCH_3$, $SO_2CH_3$, $ONO_2$, $NP_2$, $N_3$, $NH_2$, heterocycloalkyl, heterocycloalkaryl, aminoalkylamino, polyalkylamino or substituted silyl, an RNA cleaving group, a group for improving the pharmacokinetic properties of an oligonucleotide, or a group for improving the pharmacodynamic properties of an oligonucleotide.

In general, the coupling reaction entails generating a carbon-centered radical appended at either a 3' or 5' position of one synthon, and reacting that radical with a radical acceptor group appended to a 5' or 3' position of the other synthon. This reaction scheme preferably is repeated a number of times to produce a desired nucleosidic sequence.

DETAILED DESCRIPTION OF THE INVENTION

The term "nucleoside" as used in connection with this invention refers to a unit made up of a heterocyclic base and its sugar. The term "nucleotide" refers to a nucleoside having a phosphate group on its 3' or 5' sugar hydroxyl group. Thus nucleosides, unlike nucleotides, have no phosphate group. "oligonucleotide" refers to a plurality of joined nucleotide units formed in a specific sequence from naturally occurring bases and pentofuranosyl groups joined through a sugar group by native phosphodiester bonds. This term refers to both naturally occurring and synthetic species formed from naturally occurring subunits.

The compounds of the invention generally can be viewed as "oligonucleotide analogs", that is, compounds which function like oligonucleotides but which have non-naturally occurring portions. Oligonucleotide analogs can have altered sugar moieties, altered base moieties or altered inter-sugar linkages. For the purposes of this invention, an oligonucleotide analog having non-phosphodiester bonds, i.e., an altered inter-sugar linkage, is considered to be an "oligonucleoside." The term "oligonucleoside" thus refers to a plurality of nucleoside units joined by linking groups other than native phosphodiester linking groups. The term "oligomers" is intended to encompass oligonucleotides, oligonucleotide analogs or oligonucleosides. Thus, in speaking of "oligomers" reference is made to a series of nucleosides or nucleoside analogs that are joined via either natural phosphodiester bonds or other linkages, including the four atom linkers of this invention. Although the linkage generally is from the 3' carbon of one nucleoside to the 5' carbon of a second nucleoside, the term "oligomer" can also include other linkages such as 2'–5' linkages.

Oligonucleotide analogs also can include other modifications consistent with the spirit of this invention, particularly modifications that increase nuclease resistance. For example, when the sugar portion of a nucleoside or nucleotide is replaced by a carbocyclic moiety, it is no longer a sugar. Moreover, when other substitutions, such a substitution for the inter-sugar phosphorodiester linkage are made, the resulting material is no longer a true nucleic acid species. All such compounds are considered to be analogs. Throughout this specification, reference to the sugar portion of a nucleic acid species shall be understood to refer to either a true sugar or to a species taking the structural place of the sugar of wild type nucleic acids. Moreover, reference to inter-sugar linkages shall be taken to include moieties serving to join the sugar or sugar analog portions in the fashion of wild type nucleic acids.

This invention concerns modified oligonucleotides, i.e., oligonucleotide analogs or oligonucleosides, and methods for effecting the modifications. These modified oligonucleotides and oligonucleotide analogs exhibit increased stability relative to their naturally occurring counterparts. Extracellular and intracellular nucleases generally do not recognize and therefore do not bind to the backbone-modified compounds of the invention. In addition, the neutral or positively charged backbones of the present invention can be taken into cells by simple passive transport rather than by complicated protein-mediated processes. Another advantage of the invention is that the lack of a negatively charged backbone facilitates sequence specific binding of the oligonucleotide analogs or oligonucleosides to targeted RNA, which has a negatively charged backbone and will repel similarly charged oligonucleotides. Still another advantage of the present invention is it presents sites for attaching functional groups that initiate cleavage of targeted RNA.

The modified internucleoside linkages of this invention preferably replace naturally-occurring phosphodiester-5'-methylene linkages with four atom linking groups to confer nuclease resistance and enhanced cellular uptake to the resulting compound. Preferred linkages have structure $CH_2-R_A-NR_1-CH_2$, $CH_2-NR_1-R_A-CH_2$, $R_A-NR_1-CH_2-CH_2$ or $NR_1-R_A-CH_2-CH_2$ where $R_A$ is O or $NR_2$.

Generally, these linkages are prepared by functionalizing the sugar moieties of two nucleosides which ultimately are to be adjacent to one another in the selected sequence. In a 4' to 3' sense, an "upstream" synthon such as structure II is modified at its terminal 3' site, while a "downstream" synthon such as structure III is modified at its terminal 4' site. More specifically, the invention provides efficient, stereoselective syntheses of oligonucleosides via intermolecular radical addition. The radical addition reaction can be divided in two steps. The first step involves generation of an initial radical, which undergoes the desired reaction. The second step involves removal of the radical from the reaction before the occurrence of an intervening, undesired reaction such as cross coupling. In certain embodiments, the linkages of the invention are prepared by providing donor synthons having structure IIa or IIIa:

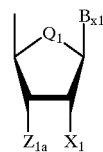

IIa

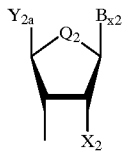

wherein $Z_{1a}$, and $Y_{2a}$ have structure $CH_2$—$R_B$ or $R_B$ where $R_B$ is a radical generating group, generating a radical centered at $Z_{1a}$ or $Y_{2a}$, and then forming a 3'–5' linkage by reacting radical-bearing donor synthons IIA and IIIa, respectively, with acceptor synthons IIIb and IIb:

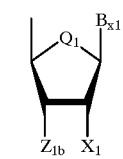

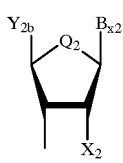

wherein either $Z_{1b}$ and $Y_{2b}$ have structure $R_A N = CH_2$ or $CH_2$—$R_A N = CH_2$ where $R_A$ is O or $NR_2$.

$B_{X1}$ and $B_{X2}$ can be nucleosidic bases selected from adenine, guanine, uracil, thymine, cytosine, 2-aminoadenosine or 5-methylcytosine, although other non-naturally occurring species can be employed to provide stable duplex or triplex formation with, for example, DNA. Representative bases are disclosed in U.S. Pat. No. 3,687,808 (Merigan, et al.), which is incorporated herein by reference.

$Q_1$ and $Q_2$ can be S, $CH_2$, CHF, $CF_2$ or, preferably, O. See, e.g., Secrist, et al., Abstract 21, Synthesis and Biological Activity of 4'-Thionucleosides, Program & Abstracts, Tenth International Roundtable, Nucleosides, Nucleotides and their Biological Applications, Park City, Utah, Sep. 16–20, 1992.

$X_1$ and $X_2$ are, independently, H, OH, $C_1$ to $C_{10}$ lower alkyl, substituted lower alkyl, alkaryl or aralkyl, F, Cl, Br, CN, $CF_3$, $OCF_3$, OCN, O-alkyl, S-alkyl, N-alkyl, O-alkenyl, S-alkenyl, N-alkenyl, $SOCH_3$, $SO_2CH_3$, $ONO_2$, $NO_2$, $N_3$, $NH_2$, heterocycloalkyl, heterocycloalkaryl, aminoalkylamino, polyalkylamino or substituted silyl, an RNA cleaving group, a group for improving the pharmacokinetic properties of an oligonucleotide, or a group for improving the pharmacodynamic properties of an oligonucleotide. It is preferred that X is H or OH, or, alternatively F, O-alkyl or O-alkenyl, especially where Q is O. Preferred alkyl and alkenyl groups have from 1 to about 10 carbon atoms.

$Y_1$ and $Z_2$ can be H, hydroxyl, aminomethyl, hydrazinomethyl, hydroxymethyl, C-formyl, phthalimidohydroxymethyl, aryl-substituted imidazolidino, aminohydroxylmethyl, ortho-methylaminobenzenethio, methylphosphonate, methylalkylphosphonate, a nucleoside, a nucleotide, an oligonucleotide, an oligonucleoside, or a hydroxyl-protected or amine-protected derivative thereof. Preferably, $Y_1$ is a protected hydroxymethyl group or a nucleoside or oligonucleoside attached by, for example, a phosphodiester-5'-methylene linkage or some other four atom linking group, and $Z_2$ is a protected hydroxyl group or a nucleoside or oligonucleoside attached by, for example, a phosphodiester-3'-hydroxyl linkage or some other four atom linking group.

It is preferred that the oligonucleotide analogs of the invention comprise from about 5 to about 50 subunits 35 having the given structure (i.e., n=5–50). While each subunit of the oligonucleotide analogs can have repetitive structure I, such need not be the case. For example, the subunits can have alternating or more random structures.

The methods of the invention generally involve "non-chain" processes. In nonchain processes, radicals are generated by stoichiometric bond homolysis and quenched by selective radical-radical coupling. It has been found that bis(trimethylstannyl)benzopinacolate and bis(tributylstannyl)benzopinacolate (see Comprehensive Organic Synthesis: Ed. by B. M. Trost & J. Fleming, Vol. 4, pp 760)—persistent radicals—can be used to enhance the radical-radical coupling and reduce cross-coupling. It will be recognized that a persistent radical is one that does not react with itself at a diffusion-controlled rate. Hillgartner, et al., Liebigs. Ann. Chem. 1975, 586, disclosed that on thermolysis (about 80° C.) pinacolate undergoes homolytic cleavage to give the suspected persistent radical ($Ph_2C\cdot OSnMe_3$), which stays in equilibrium with benzophenone and the trimethylstannyl radical ($Me_3Sn\cdot$). It is believed that the $Me_3Sn\cdot$ radical abstracts iodine from radical precursors such as 3'-deoxy-3'-iodo nucleosides or 5'-deoxy-5'-iodo nucleoside derivatives to give 3' or 5' nucleoside radicals. The nucleoside radicals then add to, for example, oxime ether acceptors such as 3'- or 5'-deoxy-3' or 5'-methyleneamino-oxy nucleoside derivatives to give a dimeric nucleoside containing a dephospho internucleoside linkage.

The concentration of the persistent radical is an important variable in these reactions because at high concentrations the initial radical can be trapped by coupling prior to addition, and at low concentrations the adduct radical can begin to telomerize. It is believed that a 3 molar equivalent excess of pinacolate provides satisfactory results for such couplings. The efficiency of radical reactions are highly dependent on the concentration of the reagents in an appropriate solvent. Preferably, the solvent contains, for example, benzene, dichlorobenzene, t-butylbenzene, t-butyl alcohol, water, acetic acid, chloroform, carbon tetrachloride, and mixtures thereof. The solvent should contain a combined concentration of about 0.1 to about 0.4 moles/liter of radical precursor and acceptor, preferably about 0.1 to about 0.2 moles/liter, more preferably about 0.2 moles/liter. It has been found that best results are obtained using benzene solutions containing about 0.2 moles/liter of radical precursor and acceptor.

As exemplified in Scheme I, chain elongation in a 5' to 3' sense can be achieved generally by refluxing a 0.2–0.4 molar solution of 5'-deoxy-5'-iodo-3'-0-phthalimido nucleoside 102 (R'=hydroxyl protecting group, R"=phthalimido), 3,-deoxy-3'-methylene amino-oxy-5'-protected nucleoside 101, and bis(trimethylstannyl)-benzopinacolate in benzene under argon for 8 h to yield dimeric nucleoside 103 ($L_1$—$L_2$—$L_3$—$L_4$=O—NH—$CH_2$—$CH_2$) in 35% yield after urification by silica gel chromatography. This dimer was ethylated following standard procedures as for instance utilizing aqueous formaldehyde (20% solution) to furnish N-alkylated 104 ($L_2$=N—$CH_3$) in high yield. Further hydrazinolysis of and formulation of the product will furnish 3'-oxime ether 105 (R"=N=CH$_2$), which is ready for another round of radical coupling. Thus, coupling this dimer with bifunctional nucleoside 102 will provide trimer 106 (L$_{1a}$—L$_{2a}$—L$_{3a}$—L$_{4a}$=O—N(H)—CH$_2$—CH$_2$, n=1). In a similar manner, trimer 106 can undergo another round of coupling to furnish a tetrameric nucleoside. Repetitive coupling of this type will provide an oligomer of desired length.

Chain elongation can be terminated at any time during the described method. For example, coupling of dimer ether 105 with a 5'-deoxy-5'-iodo-3'-protected nucleoside will furnish trimer 107 (L$_{2a}$=N—CH$_3$), which could be N-methylated (L$_2$=N—CH$_3$) and deblocked at its 3' and 5' ends to yield deprotected trimer 108 (R'=R"=H).

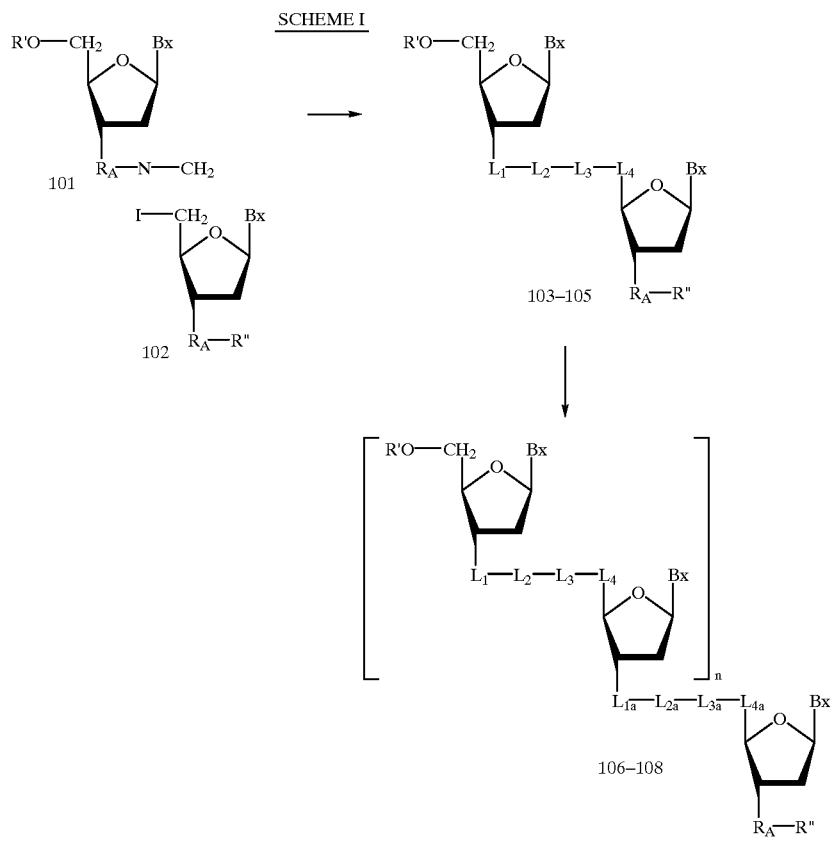

SCHEME I

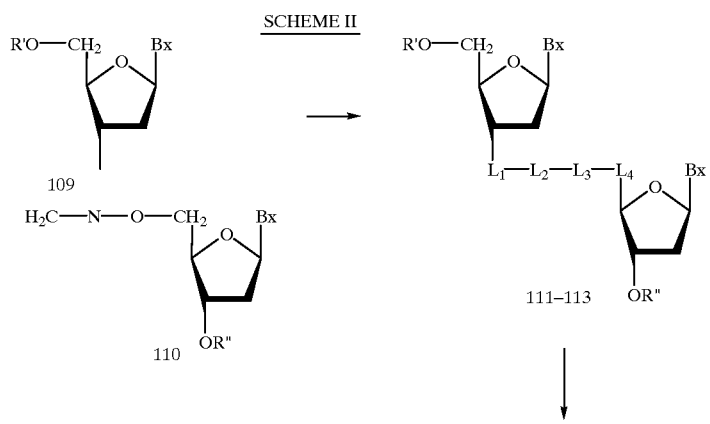

SCHEME II

-continued

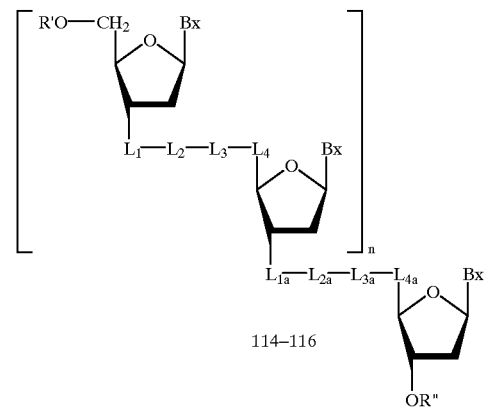

114–116

As exemplified in Scheme II, chain elongation in a 3' to 5' sense can be achieved generally by refluxing a concentrated (0.2 to 0.3 molar) solution of 3'-deoxy-3'-iodo-5'-O-phthalimido nucleoside 109, 5'-deoxy-5' [(methyleneamino)oxy]-3'-protected nucleoside 110, and bis(trimethylstannyl) benzopinacolate in benzene under argon for 8 h to yield dimeric nucleoside 111 ($L_1$—$L_2L_3$—$L_4$=$CH_2$—NH—O—$CH_2$, R'=hydroxyl protecting group, R"=phthalimido) in 45% yield after purification by silica gel chromatography. Dimer 111 was methylated following standard procedures to furnish N-alkylated 112 ($L_2$=N—$CH_3$) in good yield. Subsequently, hydrazinolysis of 112, followed by formylation of the product will furnish 113 (R'=N=$CH_2$). Dimer 113 can undergo another round of radical coupling with 109 to yield trimeric nucleoside 114 ($L_{1a}$—$L_{2a}$—$L_{3a}$—$L_{4a}$=O—N(H)—$CH_2$—$CH_2$, n=1). The latter compound could be N-methylated to yield 115 ($L_{2A}$=N—$CH_3$). A repetitive set of reactions such as hydrazinolysis, formylation, and coupling would result in an oligomer of desired length containing modified backbones. Chain elongation can be terminated at any point by coupling with 3'-deoxy-3'-iodo-5'-O-protected nucleoside 109. For example, the latter compound will couple with 113, and the product on methylation ($L_2$=N—$CH_3$) and deblocking will furnish trimeric nucleoside 116 (R'=R"=H).

A more random type of elongation-can be effected by deblocking and iodinating nucleoside 104 selectively at its 3' end to produce nucleoside 117a (R'=O-blocking group, R"=I). Coupling of 117a with 110 via 3'-elongation furnishes trimeric nucleoside 118a ($L_2$=N—$CH_3$ and $L_{2a}$=NH). Methylation and complete deblocking of 118a provides 118b (R'=R"=OH and $L_1$=$L_2$=N—$CH_3$). Alternatively, deblocking and iodinating nucleoside 112 selectively at its 5' end produces nucleoside 119a (R'=I, R"=O-blocking group). Coupling of 119a with 101 via 5'-elongation furnishes trimeric nucleoside 118a. Methylation and complete deblocking provides 118b.

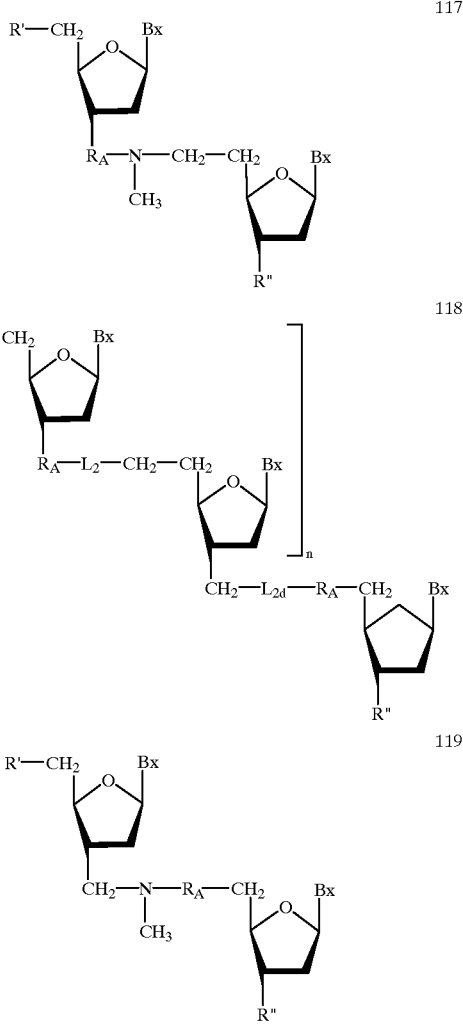

A wide range of achiral and neutral oligonucleosides containing mixed backbones can be prepared by these "random" methods. Backbone complexity can be enhanced further by selectively incorporating phosphodiester linkages to, for example, increase water solubility. (See, e.g., Example 27). Also, coupling 5'-O-dimethyoxytritylated dimeric nucleoside 117b (R'=ODMTr, R"=OH) or trimeric nucleoside 118c (R"=ODMTr, R"=OH, L$_2$=N—CH$_3$ and L$_{2a}$=NH) to CPG via a succinyl linker (see, e.g., *Nucleic Acids Research* 1990, 18, 3813) provides CPG-bound compounds that can be used as 3'-terminal units for automated synthesis. The placement of such dimeric or trimeric oligonucleosides at the 3'-end of an antisense oligomer will result in the protection of the antisense molecules from attack by 3'-exonucleases typically found in human serum.

In summary, the chain elongation methods of the invention require essentially two types of nucleoside building blocks. The first is a monofunctional nucleoside with one reactive group for coupling at 3' or 5' end and an appropriate blocking group at the remaining end. The second is a bifunctional nucleoside which has a reactive coupling group at 3' or 5 end and a protected reactive coupling group at the other end.

The methods of the invention can be modified for use with either solution-phase or solid-phases techniques. For example, the compounds of the invention can be synthesized using controlled pore glass (CPG) supports and standard nucleic acid synthesizing machines such as Applied Biosystems Inc. 380B and 394 and Milligen/Biosearch 7500 and 8800s. Each new nucleoside is attached either by manual manipulation or by automated techniques.

A wide variety of protecting groups can be employed in the methods of the invention. See, e.g., Beaucage, et al., *Tetrahedron* 1992, 12, 2223. In general, protecting groups render chemical functionality inert to specific reaction conditions, and can be appended to and removed from such functionality in a molecule without substantially damaging the remainder of the molecule. Representative hydroxyl protecting groups include t-butyldimethylsilyl (TBDMSi), t-butyldiphenylsilyl (TBDPSi), dimethoxytrityl (DMTr), monomethoxytrityl (MMTr), and other hydroxyl protecting groups as outlined in the above-noted Beaucage reference.

Scheme III illustrates certain abbreviations used for blocking groups in other of the schemes. Scheme III further shows the synthesis of 3'-O-amino and 3'-O-methyleneamino nucleosides via a Mitsunobu reaction utilizing N-hydroxylphthalimide and methylhydrazine to generate an —O—NH$_2$ moiety on a sugar hydroxyl. The —O—NH$_2$ group can then be derivatized to a —O-methyleneamino moiety. These reactions are exemplified in Examples 5, 6, 7, 9 and 18.

The reactions of Examples 5, 6, 7 and 9 represent an improved synthesis of 3'-O-NH$_2$ nucleosides. In forming —O—NH$_2$ moieties on sugars, it is theoretically possible to displace a leaving group, such as a tosyl group, with hydroxylamine. However, Files, et al., *J. Am. Chem. Soc.* 1992, 14, 1493, have shown that such a displacement leads to a preponderance of —NHOH moieties and not to the desired —O—NH$_2$ moieties. Further, the reaction sequence of Examples 5, 6, 7 and 9 represents an improved synthesis compared to that illustrated in European Patent Application 0381335. The synthetic pathway of that patent application requires the use of a xylo nucleoside as the staring material. Xylo nucleosides are less readily obtainable than the ribonucleoside utilized in Examples 5, 6, 7 and 9.

Scheme VIII illustrates a synthetic scheme utilized to prepare dimers, trimers, and other, higher-order oligonucleosides having homogenous linkages between nucleosides. In this scheme, nucleosides 10 and 12 are linked to form an iminomethylene linkage as exemplified in Example 11. Advantageous use of the alkylating-5' terminus deblocking step of Scheme VI is effected to remove the blocking group at the 5' terminus of the dimeric oligonucleoside 14, as in Example 12. Using the iodination reaction of Scheme IV, the dimer then is converted to a 5' terminus iodo intermediate, as in Example 14. A further 3'-O-methyleneamino nucleosidic unit 10 then can be added to the dimer to form a trimer, as in Example 15, followed by deblocking and alkylation, as in Example 16. This reaction sequence can be repeated any number of times to form a higher order oligonucleoside. The oligonucleoside is deblocked at the 3' terminus, as is exemplified for the dimer in Example 13 or the tetramer in Example 17.

Scheme IX illustrates a radical reaction that forms a linkage having a pendant hydroxyl moiety. This is exemplified in Example 21. The pendant OH group can be oxidized to an =O using Moffatt oxidization conditions. Alternatively, the pendant OH moiety can be cyclized to the nitrogen atom of the linkage to form either a five or a six membered heterocyclic ring. The formation of a linkage incorporating a six atom ring is exemplified in Example 22. A five atom ring would be formed utilizing condition analogous to those of Neumeyer, et al., *J. Org. Chem.* 1973, 38, 2291, to add phosgene in the presence of a base such as triethylamine or diethylphenylamine in toluene at a temperature of about 60 to about 80° C.

SCHEME III

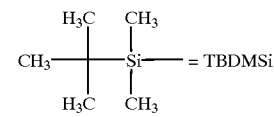

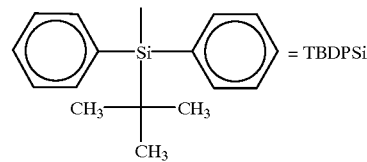

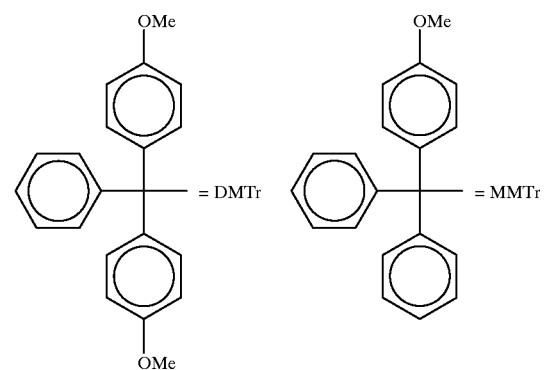
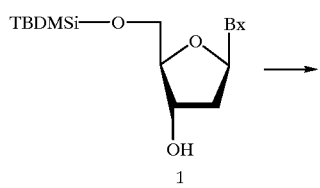
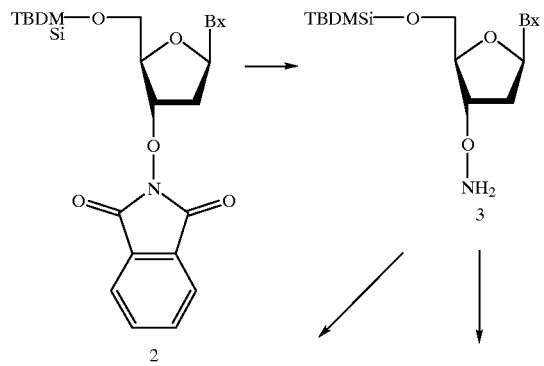
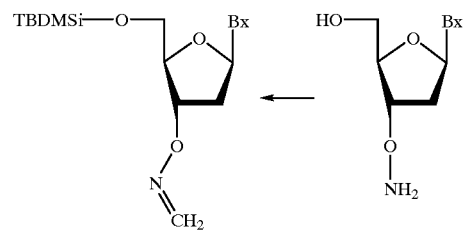
| 10 Bx = Thymine | 4 Bx = Thymine |
| 27 Bx = Adenine | 24 Bx = Adenine |
| 28 Bx = Cytosine | 25 Bx = Cytosine |
| 29 Bx = Guanine | 26 Bx = Guanine |
SCHEME IV
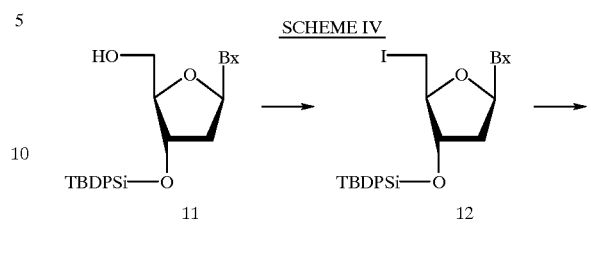
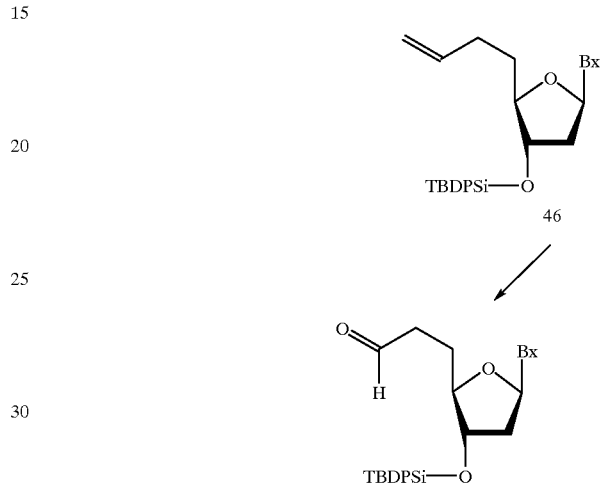
SCHEME V
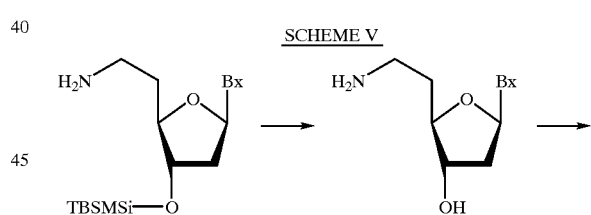

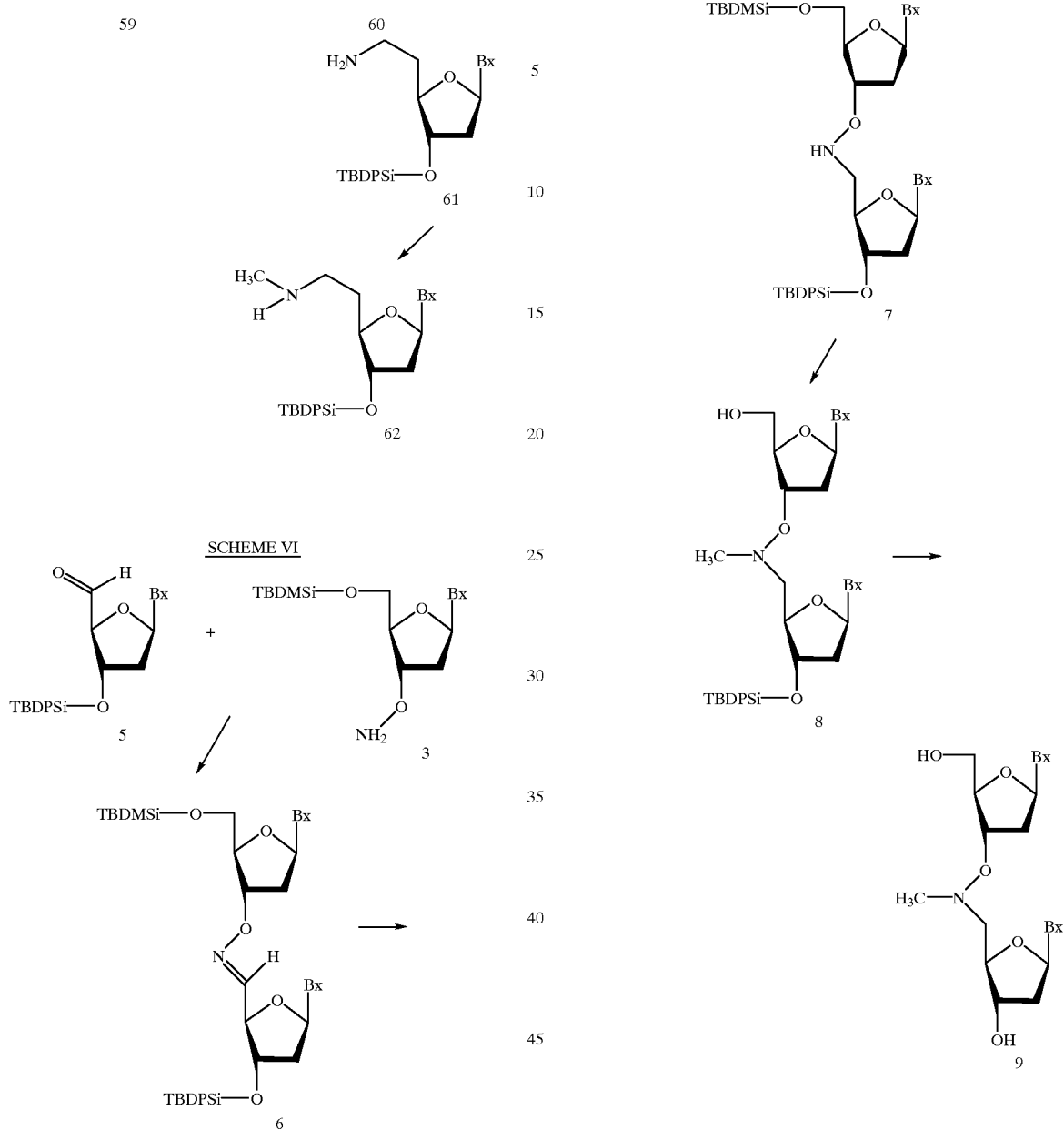

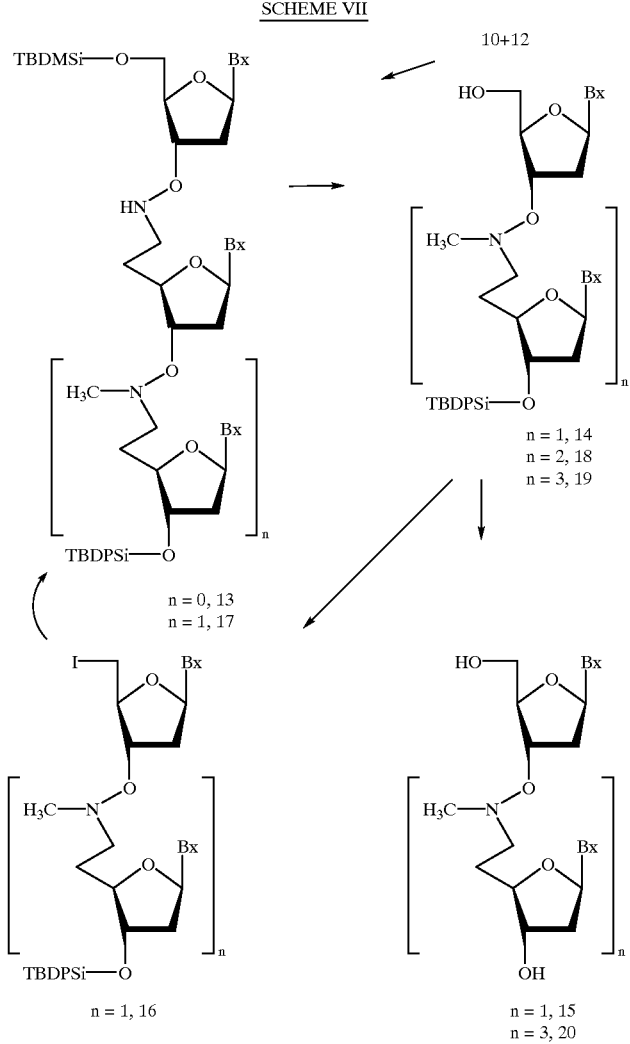
SCHEME VII
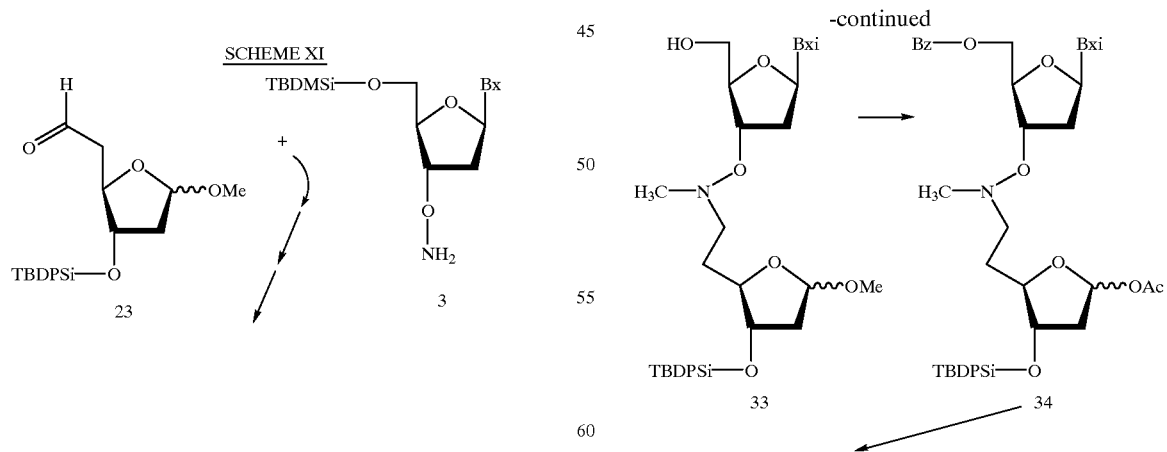
SCHEME XI

21
-continued
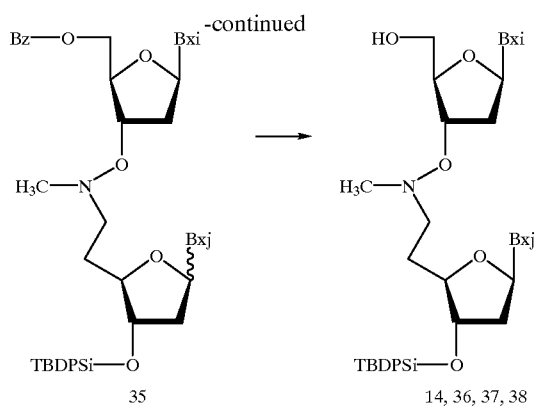
22
-continued
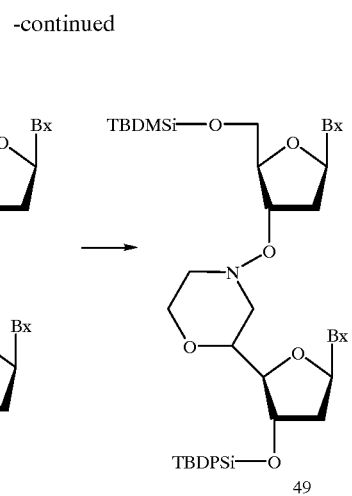
SCHEME IX
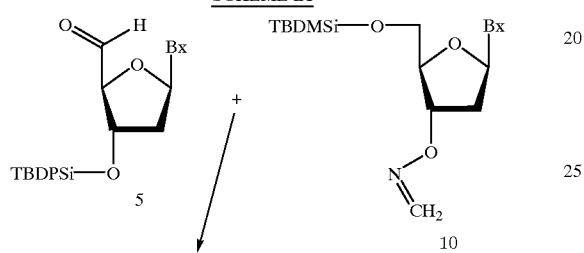
SCHEME X
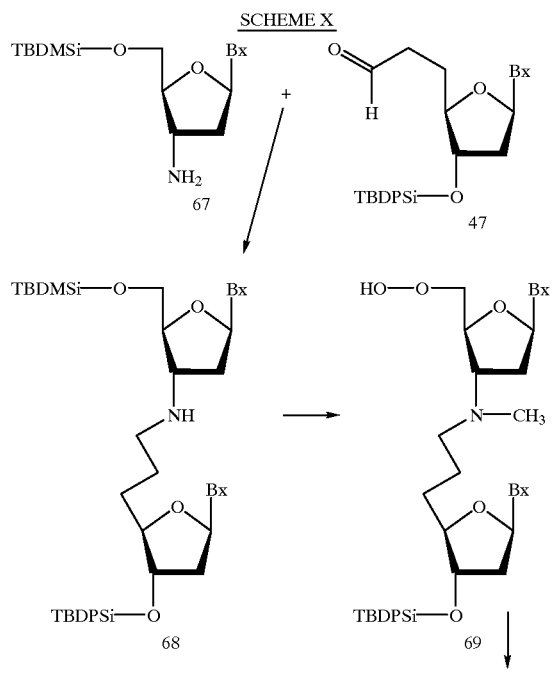

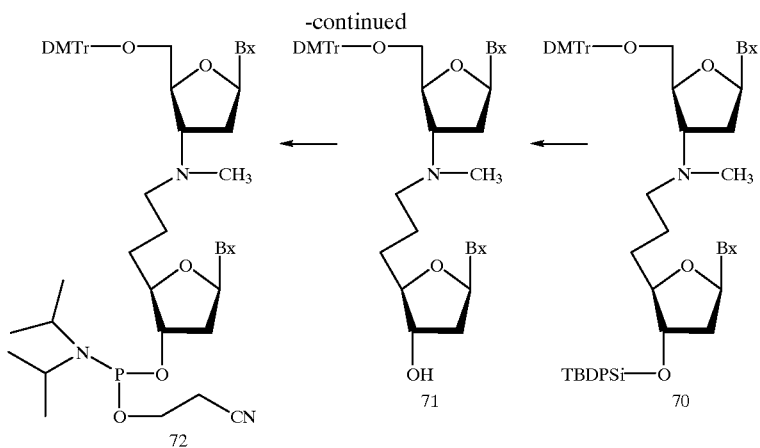

-continued 71  70  72

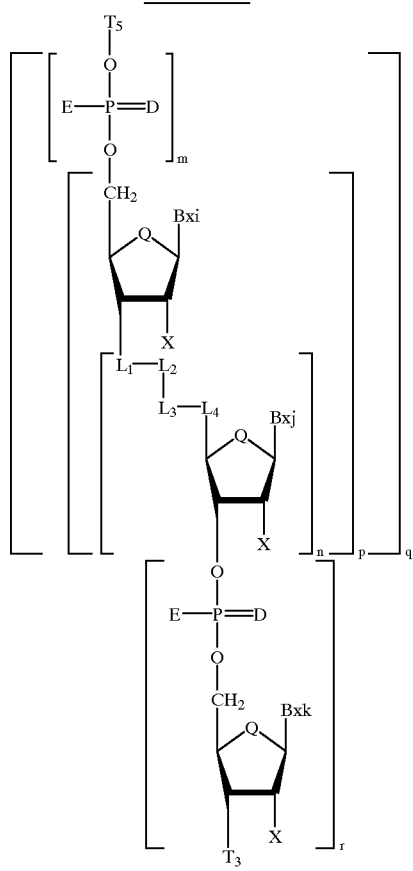

SCHEME XI

The compounds of this invention can be used in diagnostics, therapeutics, and as research reagents and kits. For therapeutic use the oligonucleotide analog is administered to an animal suffering from a disease modulated by some protein. It is preferred to administer to patients suspected of suffering from such a disease an amount of oligonucleotide analog that is effective to reduce the symptomology of that disease. One skilled in the art can determine optimum dosages and treatment schedules for such treatment regimens.

It is preferred that the RNA or DNA portion which is to be modulated be preselected to comprise that portion of DNA or RNA which codes for the protein whose formation or activity is to be modulated. The targeting portion of the composition to be employed is, thus, selected to be complementary to the preselected portion of DNA or RNA, that is to be an antisense oligonucleotide for that portion.

In accordance with one preferred embodiment of this invention, the compounds of the invention hybridize to HIV mRNA encoding the tat protein, or to the TAR region of HIV mRNA. In another preferred embodiment, the compounds mimic the secondary structure of the TAR region of HIV mRNA, and by doing so bind the tat protein. Other preferred compounds complementary sequences for herpes, papilloma and other viruses.

It is generally preferred to administer the therapeutic agents in accordance with this invention internally such as orally, intravenously, or intramuscularly. Other forms of administration, such as transdermally, topically, or intralesionally may also be useful. Inclusion in suppositories may also be useful. Use of pharmacologically acceptable carriers is also preferred for some embodiments.

This invention is also directed to methods for the selective binding of RNA for research and diagnostic purposes. Such selective, strong binding is accomplished by interacting such RNA or DNA with compositions of the invention which are resistant to degradative nucleases and which hybridize more strongly and with greater fidelity than known oligonucleotides or oligonucleotide analogs.

Additional objects, advantages, and novel features of this invention will become apparent to those skilled in the art upon examination of the following examples thereof, which are not intended to be limiting, wherein parts and percents are by weight unless otherwise indicated. For NMR analysis of dimers and other higher oligonucleosides, monomeric units are numbered (e.g., $T_1$, $T_2$) from the 5' terminus towards the 3' terminus nucleoside. Thus, the 5' nucleoside of a T-T dimer is $T_1$ and the 3' nucleoside is $T_2$.

General Procedures

Radical Addition Reaction

A suspension of radical precursor (1–3 eq.), radical acceptor (1 eq.), persistent radical (3 eq.) in benzene (0.2–0.4 mol. solution) was carefully degassed under vacuum (water aspirator) and flushed with argon (3–20 times). The reaction mixture was heated at 80–85° C. for 6–12 h under argon while stirring. The suspension dissolves to give a clear solution in about 1–2 h. The reaction mixture may change the color during the course of heating but remains clear all along. Completion of the reaction was judged by the disappearance of radical precursor (detected by TLC) and formation of a polar product. The reaction mixture then was cooled to room temperature and diluted with ether (five times the original volume). The fine suspension was loaded onto a prepacked silica gel column (30 g of silica per gram of product) and eluted with hexanes (100%) until most of the UV absorbing impurities were removed. The column then was eluted with a hexanes-ether gradient in which the concentration of ether gradually increased to effect a 10% increase in the polarity of the solvent. Elution with ether furnished the desired product as homogeneous material. Pooling and evaporation of appropriate fractions generally gave 40–55% yield of the desired dimeric nucleoside.

N-Alkylation of Backbone

To a stirred solution of oligonucleoside (1 eq.; containing $CH_2$—O—NH—$CH_2$ linkages) in glacial acetic acid was added an aqueous solution of HCHO (3–5 eq.; >99% HCHO) in one portion under argon. The clear solution was stirred for 5–15 min. at room temperature until no more starting material was detected by TLC. At this point dry $NaBH_3CN$ (3–6 eq.) was added in 3–6 portions under argon at room temperature under a well ventilated fume hood. Care must be taken to cool the reaction mixture if it is over 5 mmol. scale. After addition, the reaction mixture was stirred for 1–2 h at room temperature (until evolution of gas ceases). Completion of the reaction was detected by TLC, which indicated formation of a higher product, compared to the starting material. The reaction mixture was concentrated under vacuum and the residue purified by short column chromatography. Elution with a $CH_2Cl_2 \rightarrow MeOH$ gradient (increasing polarity to 10%) furnished the desired product as homogeneous material.

This procedure was applicable to a variety of substituted aldehydes which formed Schiff bases with the amino group of the linker. Subsequent reduction gave selective alkylation of the backbone. Heterocyclic or exocyclic amines of the purine/pyrimidine were not affected by this method.

Composition Analysis of Modified oligomers

Incorporation of oligonucleoside containing backbones of the invention into antisense molecules was proved by enzymatic tandem hydrolysis of modified oligomers using snake-venom phosphodiesterase followed by alkaline phosphatase. In all cases, the identity of dimeric nucleosides was proven by addition of synthetic sample and comparison on HPLC profile. The integration of the peaks of HPLC analysis demonstrated the correct gross composition of the modified oligomer.

EXAMPLE 1

Synthesis of 5'-O-Phthalimido Nucleosides

5'-O-Phthalimidothynidine

To a stirred solution of thymidine (24.22 g, 0.1 mol), N-hydroxyphthalimide (21.75 g, 0.13 mol), triphenylphosphine (34 g, 0.13 mol) in dry DMF (400 ml) was added diisopropylazodicarboxylate (30 ml, 0.15 mol) over a period of 3 h at 0° C. After complete addition the reaction mixture was warmed up to room temperature and stirred for 12 h. The solution was concentrated under vacuum (0.1 mm., <40° C.) to furnish an orange-red residue. The residual gum was washed several times with $Et_2O$ and washing were discarded. The semi-solid residue was suspended in EtOH (500 ml) and heated (90° C.) to dissolve the product. On cooling 30.98 g (80%) of 5'-Q-phthalimidothymidine was collected in 3-crops as white crystalline material, mp 233–235° C. (decomp.); $^1$H NMR (DMSO-$d_6$) δ 11.29 (s, 1, N$\underline{H}$), 7.85 (m, 4, Ar$\underline{H}$), 7.58 (s, 1, $C_6\underline{H}$), 6.20 (t, 1, $\underline{H}_{1'}$, $J_{1',2'}$=7.8 Hz, $J_{1',2''}$=6.5 Hz), 5.48 (d, 1, O$\underline{H}_{3'}$), 4.36 (m, 3, $\underline{H}_{4',5',5''}$), 4.08 (m, 1, $\underline{H}_{3'}$), 2.09–2.13 (m, 2, $\underline{H}_{2',2''}$), and 1.79 (s, 3, C$\underline{H}_3$). Anal. Calcd. for $C_{18}H_{17}O_7N_3 \cdot 0.7 H_2O$: C, 54.05; H, 4.64; N, 10.51. Found: C, 53.81; H, 4.25; N, 10.39.

2'-deozy-5'-O-phthalimidouridine

An analogous reaction on 2'-deoxyuridine gave the corresponding 2'-deoxy-5'-O-phthalimidouridine; mp 241–242°C.

2'-deozy-5'-O-phthalimidocytidine

An analogous reaction on 2'-deoxycytidine gave the corresponding 2'-deoxy-5'-O-phthalimidocytidine in 40% yield.

2'-deozy-5'-O-phthalimidoadenosine

An analogous reaction on 2'-deoxyadenosine gave the corresponding 2'-deoxy-5'-O-phthalimidoadenosine in 55% yield.

2'-deoxy-5'-O-phthalimidoguanosine

An analogous reaction on 2'-deoxyguanosine gave the corresponding 2'-deoxy-5'-O-phthalimidoguanosine in 25% yield.

EXAMPLE 2

Synthesis of 5'-O-phthalimido-3'-O-(t-butyldiphenyl-silyl) thymidine and 2'-deozy-5'-O-phthalisido-3'-O-(t-butyldiphenylsilyl)uridine 3'-O-(t-butyldiphenylsilyl)-5'-O-phthalimidothysidine A mixture of 5'-O-phthalimidothymidine (8.54 g, 22 mmol), t-butyldiphenylsilylchloride (6.9 ml, 26.5 mmol), imidazole (3.9 g, 57.3 mmol) and dry DMF (130 ml) was stirred at room temperature for 16 h under argon. The reaction mixture was poured into ice-water (600 ml) and the solution was extracted with $CH_2Cl_2$ (2×400 ml). The organic layer was washed with water (2×250 ml) and dried ($MgSO_4$). The $CH_2Cl_2$ layer was concentrated to furnish a gummy residue which on purification by silica gel chromatography (eluted with EtOAc:Hexanes; 1:1, v/v) furnished 12.65 g (92%) of 3'-O-(t-butyldiphenylsilyl)-5'-O-phthalimidothymidine as crystalline material (mp 172–173.5° C.). $^1$H NMR (DMSO-$d_6$) δ 11.31 (s, 1, N$\underline{H}$), 7.83 (m, 4, Ar$\underline{H}$), 7.59 (m, 4, TBDPh$\underline{H}$), 7.51 (s, 1, $C_6\underline{H}$), 7.37–7.45 (m, 6, TBDPh$\underline{H}$), 6.30 (dd, 1, $\underline{H}_{1'}$, $J_{1',2'}$=8.8 Hz, $J_{1',2''}$=5.6 Hz), 4.55 (m, 1, $\underline{H}_{4'}$), 4.15 (m, 1, $\underline{H}_{3'}$), 3.94–4.04 (m, 2, $\underline{H}_{5',5''}$) 2.06–2.13 (m, 2, $\underline{H}_{2',2''}$), 1.97 (s, 3, C$\underline{H}_3$), 1.03 (s, 9, C(C$\underline{H}_3$)$_3$). Anal. Calcd. for $C_{34}H_{35}O_7N_3Si$: C, 65.26; H, 5.64; N, 6.71. Found: C, 65.00; H, 5.60; N, 6.42.

3'-O-(t-butyldiphenylsilyl)-2'-deoy-5'-O-phthalimidouridine

An analogous reaction of 2'-deoxy-5'-O-phthalimidouridine will give the corresponding 3'-O-(t-butyldiphenylsilyl)-2'-deoxy-5'-O-phthalimidouridine.

3'-O-(t-butyldiphenylsilyl)-2'-deoxy-5'-O-phthalimidocytidine

An analogous reaction of 2'-deoxy-5'-O-phthalimidocytidine gave the corresponding 3'-O-(t-butyldiphenylsilyl)-2'-deoxy-5'-O-phthalimidocytidine in 65% yield.

3'-O-(t-butyldiphenylsilyl)-2'-deoxy-5'-O-phthalimidoadenosine

An analogous reaction of 2'-deoxy-5'-O-phthalimidoadenosine gave the corresponding 3'-O-(t-butyldiphenylsilyl)-2'-deoxy-5'-O-phthalimidoadenosine in 70% yield.

3'-O-(t-butyldiphanyluilyl)-2'-deoxy-5'-O-phthalimidoguanosine

An analogous reaction of 2'-deoxy-5'-O-phthalimidoguanosine gave the corresponding 3'-O-(t-butyldiphenylsilyl)-2'-deoxy-5'-O-phthalimidoguanosine in 65% yield.

EXAMPLE 3
Synthesis of 5'-O-amino nucleoside
5'-O-amino-3'-O-(t-butyldiphenylsilyl)thysidine To a stirred solution of 3'-O-(t-butyldiphenyl-silyl)-5'-O-phthalimidothymidine (10 g, 16 mmol) in dry $CH_2Cl_2$ (100 ml) was added methylhydrazine (1.3 ml, 24 mmol) under argon at room temperature and solution stirred for 12 h. The solution was cooled (0° C.) and filtered. The white residue was washed with $CH_2Cl_2$ (2×25 ml) and combined filtrates were evaporated to furnish gummy residue. The residue on purification by silica gel column chromatography (elution with $CH_2Cl_2$:MeOH, 98:2, v/v) furnished 7.03 g (89%) of 5'-O-amino-3'-O-(t-butyldiphenylsilyl)thymidine that crystallized from $CH_2Cl_2$/MeOH mp 141–143° C. $^1$H NMR (DMSO-$d_6$) δ 11.29 (s, 1, N$\underline{H}$), 7.42–7.62 (m, 11, TBDPh$\underline{H}$, $C_6$ $\underline{H}$), 6.25 (dd, 1, $\underline{H}_{1'}$, $J_{1',2'}$=8.4 Hz, $J_{1',2''}$=6.3 Hz), 6.02 (s, 2, N$\underline{H}_2$), 4.35 (m, 1, $\underline{H}_{4'}$), 4.04 (m, 1, $\underline{H}_{3'}$), 3.34–3.51 (m, 2, $\underline{H}_{5',5''}$), 2.04 (m, 2, $\underline{H}_{2',2''}$), 1.73 (s, 3, C$\underline{H}_3$), 1.03 (s, 9, C(C$\underline{H}_3$)$_3$). Anal. Calcd. for $C_{26}H_{33}O_5N_3Si$: C, 63.00; H, 6.71; N, 8.48. Found: C, 62.85; H, 6.67; N, 8.32.

EXAMPLE 4
Synthesis of methylated [3'—$CH_2$—N($CH_3$)—O—$CH_2$—5'] linked oligonucleoside
3'-De(ozyphosphinico)-3'-[methylene(methyl-imino)]thymidylyl-(3'→5') thymidine To a stirred solution of 3'-de(oxyphosphinico)-3'-(methyleneimino)thymidylyl-(3'→5')-3'-O-(t-butyldiphenylsilyl)thymidine dimer (0.99 g, 1 mmol) in glacial AcOH (10 ml) was added aqueous HCHO (20%, 3 ml). The solution was stirred for 5 min. at room temperature and to this was added $NaBH_3CN$ (0.19 g, 3 mmol) in 3-portions under argon at room temperature. The addition of $NaBH_3CN$ (0.19 g) was repeated once more and solution was further stirred for 1 h. The reaction mixture was concentrated to furnish crude 3'-de(oxyphosphinico)-3'-[methylene(methylimino)]-thymidylyl-(3'→5')-3'-O-(t-butyldiphenylsilyl)thymidine dimer, which on deblocking (n$Bu_4$NF/THF, HCl/MeOH) furnished the title compound, 3'-de(oxyphosphinico)-3'-[methylene-(methylimino)]thymidylyl-(3'→5') thymidine, (0.44 g, 87%) as white solids. The 3'-de(oxyphosphinico)-3'-[methylene-(methylimino)]thymidylyl-(3'→5') thymidine dimer was further purified by preparative HPLC furnishing an analytically pure sample. $^1$H NMR (DMSO-$d_6$) δ 11.30 and 11.24 (2s, 2, 2N$\underline{H}$), 7.82 and 7.50 (2s, 2, 2$C_6\underline{H}$), 6.15 (pseudo t, 1, T2 $\underline{H}_{1'}$, $J_{1',2'}$=6.3 Hz, $J_{1',2''}$=7.3 Hz), 6.00 (pseudo t, 1, T1 $\underline{H}_{1'}$, $J_{1',2'}$=4.2 Hz, $J_{1',2''}$=6.1 Hz), 5.31 (m, 1, T2 O$\underline{H}$), 5.08 (m, 1, T1, O$\underline{H}$), 4.17 (m, 1, T2 $\underline{H}_{3'}$), 3.88 (m, 1, T2 $\underline{H}_{4'}$), 3.57–3.83 (m, 5, T1 T2 $\underline{H}_{4=,5''}$, T1 $\underline{H}_{4'}$), 2.69 (m, 2, T1 $\underline{H}_{3''}$), 2.57 (s, 3, N—C$\underline{H}_3$), 2.50 (m, 1, T1 $\underline{H}_{3'}$), 2.05–2.14 (m, 4, T1 T2 $\underline{H}_{2',2''}$), 1.79 and 1.76 (2s, 6, 2 C$\underline{H}_3$). MS FAB: M/z 510 (M+H)$^+$. Anal. Calcd. for $C_{23}H_{31}N_5O_9·H_2O$: C, 50.09; H, 6.31; N, 13.28. Found: C, 50.05; H, 6.21, N, 13.08.

EXAMPLE 5
5'-O-(t-Butyldiaothylsilyl)-3'-O-Phthalimidothynidine, 2

To a solution of 5'-O-t-butyldimethylsilylthymidine [1, 21.36 g, 60 mmol, prepared according to the procedure of Nair, et al., *Org. Prep. Procedures Int*. 1990, 22, 57 in dry THF (750 ml)], triphenylphosphine (17.28 g, 66 mmol) and N-hydroxyphthalimide (10.74 g, 66 mmol) were added. The solution was cooled to 0° C. and diisopropylazodicarboxylate (15.15 g, 75 mmol) was added dropwise over a period of 3 hr while stirring under nitrogen. The reaction mixture was then stirred at room temperature for 12 hr. The solution was evaporated and the residue was dissolved in $CH_2Cl_2$ (750 ml), extracted with sat. $NaHCO_3$ (200 ml), and water (200 ml), dried ($MgSO_4$), filtered and concentrated to furnish yellow oily residue. Silica gel column chromatography (100% hexanes, and then hexanes:$Et_2O$ gradient to 90% $Et_2O$) of the residue gave compound 2 as a colorless glass (18.68 g, 62%); $^1$H NMR (CDCl$_3$) δ 0.05 [2s, 6, (C$\underline{H}_3$)$_2$], 0.91 [s, 9, (C$\underline{H}_3$)$_3$], 2.0 (s, 3, C$\underline{H}_3$), 2.5–2.65 (m, 2, 2'C$\underline{H}_2$), 4.05–4.2 (m, 2, 5'C$\underline{H}_2$), 4.25–4.35 (m, 1, 4'$\underline{H}$), 5.0 (m, 1, 3' $\underline{H}$), 6.15 (m, 1, 1'$\underline{H}$), 8.6 (br s, 1, N$\underline{H}$), and aromatic protons. Anal. Calcd. for $C_{24}H_{31}N_3O_7Si$: C, 57.46; H, 6.23; N, 8.37. found: C, 57.20; H, 6.26; N, 8.27.

EXAMPLE 6
3'-O-Amino-5'-O-(t-Butyldimethylsilyl)thysidine, 3

Cold methylhydrazine (1.6 ml, 30 mmol) was added to a stirred solution of 5'-O-(t-butyldimethylsilyl)-3'-O-phthalimidothymidine (2, 4.6 g, 9.18 mmol) in dry $CH_2Cl_2$ (60 ml) at 5–10° C. After 10 minutes white precipitation of 1,2-dihydro-4-hydroxy-2-methyl-1-oxophthalizine occurred. The suspension was stirred at room temperature for 1 h. The suspension was filtered and precipitate washed with $CH_2Cl_2$ (2×20 ml). The combined filtrates were concentrated and the residue purified by silica gel column chromatography. Elution with $CH_2Cl_2$:MeOH (100:0→97:3, v/v) furnished the title compound (3.40 g, 100%) as white solid. Crystallization from $CH_2Cl_1$ gave white needles, m.p. 171° C.; $^1$H NMR (CDCl$_3$) δ 0.05 [s, 6, (C$\underline{H}_3$)$_2$], 0.90 [s, 9, (C$\underline{H}_3$)$_3$], 2.22–2.58 (2m, 2, 2'C$\underline{H}_2$), 3.9–4.08 (m, 3, 5'C$\underline{H}_2$, and 3'$\underline{H}$) 4.30 (m, 1, 4'$\underline{H}$) 5.5 (br s, 2, N$\underline{H}_2$) 6.2 (m, 1, 1'$\underline{H}$) 7.45 (s, 1, $C_6\underline{H}$) 8.9 (br s, 1, N$\underline{H}$). Anal. Calcd. for $C_{16}H_{29}N_3O_5Si$: C, 51.72; H, 7.87; N, 11.32. found: C, 51.87, H, 7.81; N, 11.32.

EXAMPLE 7
3'-O-Aminothymidine, 4

3'-O-Amino-(t-butyldimethylsilyl)thymidine was deblocked with (Bu)$_4$NF/THF in standard way to furnish compound 4 (72%). Crystallized from ether/hexanes/ethanol as fine needles, mp 81° C. $^1$H NMR (Me$_2$SO-$d_6$) δ 1.78 (s, 3, C$\underline{H}_3$), 2.17 and 2.45 (2m, 2, 2'C$\underline{H}_2$), 3.70 (m, 2, 5'C$\underline{H}_2$), 3.88 (m, 1, 4'$\underline{H}$), 4.16 (m, 1, 3'$\underline{H}$), 4.8 (br s, 1, 5'O$\underline{H}$), 6.05 (dd, 1, 1'$\underline{H}$), 6.2 (br s, 2 N$\underline{H}_2$), 7.48 (s, 1, $C_6\underline{H}$), and 11.24 (br s, 1, N$\underline{H}$). Anal. Calcd. for $C_{10}H_{15}N_3O_5$: C, 46.69; H, 5.87; N, 16.33; found: C, 46.55; H, 5.91; N, 16.21.

EXAMPLE 8
3'-O-Dephosphinico-3'-O-(Methylimino)thyidylyl-(3'→5')-5,-Deoxythymidine, 9

Step 1

3'-O-Amino-5'-O-(t-butyldimethylsilyl)thymidine (3, 1.85 g, 5 mmol), 3'-O-(t-butyldimethylsilyl)thymidine-5'-aldshyde [5, 2.39 g, 5 mmol; freshly prepared by following the method of Camarasa, et al., *Nucleosides and Nucleotides* 1990, 9, 533] and ACOH (0.25 ml) were stirred together in $CH_2Cl_2$ (50 ml) solution at room temperature for 2 h. The products were then concentrated under reduced pressure to give the intermediate oxime linked dimer, compound 6.

Step 2

The residue obtained from Step 1 was dissolved in AcOH (25 ml). NaCNBH$_3$ (1.55 g, 25 mmol, in 3-portions) was added to the stirred AcOH solution at room temperature. The solution was stirred for 30 min to give the intermediate imine linked dimer, compound 7.

Step 3

Aqueous HCHO (20%, 2 ml, 66 mmol) and additional NaCNBH$_3$ (1.55 g, 25 mmol, in 3-portions) was added to the stirred reaction mixture of Step 2 at room temperature. After 2 h, the solution was diluted with EtOH (100 ml), and resulting suspension was evaporated under reduced pressure. The residue was dissolved in $CH_2Cl_2$ (150 ml) and then washed successively with 0.1 M HCl (100 ml), saturated aqueous $NaHCO_3$ (100 ml), and water (2–50 ml). The dried ($MgSO_4$) $CH_2Cl_2$ solution was evaporated to give crude methylated imine linked dimer 8.

Step 4

The residue from Step 3 was dissolved in the THF (30 ml) and a solution of $(Bu)_4NF$ (1 M in THF, 10 ml) was added while stirring at room temperature. After 1 h, the reaction mixture was evaporated under reduced pressure and the residue was purified by short column chromatography. The appropriate fractions, which eluted with $CH_2Cl_2$:MeOH (8:2, v/v) were pooled and evaporated to give compound 9 as a foam (0.74 g, 30%). $^1H$ NMR ($Me_2SO-d_6$) δ 1.78 (s, 6, 2C$H_3$), 2.10 (m, 4, 2'C$H_2$), 2.5 (s, 3, N—C$H_3$), 2.8 (m, 2, 5'-N—C$H_2$), 3.6–4.08 (5m, 6, 5'C$H_2$, 4' C$H$, 3' C$H$), 4.75 and 5.3 (2 br s, 2, 3' and 5' O$H$), 6.02 (d, 1, 1'$H$), 6.1 (t, 1, 1'$H$), 7.4 and 7.45 (2s, 2, 2C$_6H$), 11.3 (br s, 2, N$H$).

EXAMPLE 9
5'-O-(t-Butyldimethylsilyl)-3'-Deoxy-3'-[(Methyleneamino)-oxy]thymidine, 10

A solution of HCHO (20% aqueous, 1 ml) was added dropwise to a stirred solution of 3'-O-amino-5'-O-(t-butyldimethylsilyl)thymidine (3, 7.42 g, 20 mmol) in dry MeOH (400 ml) at room temperature. After 6 h, another portion of HCHO (20% aqueous, 1.5 ml) was added and stirring continued for 16 h. The resulting solution was evaporated under reduced pressure, and the residue was purified by chromatography on silica gel to give compound 10 (7.25 g, 95%) as clear foam. $^1H$ NMR ($CDCl_3$) δ 0.1 [s, 3, ($CH_3)_2$], 0.9 [s, 9, ($CH_3)_3$], 1.9 (s, 3, C$H_3$), 2.25–2.72 (m, 2, 2' C$H_2$), 3.85–4.15 (2m, 3, 5' C$H_2$, 4' $H$), 4.85 (m, 1, 3'$H$), 6.25 (dd, 1, 1'$H$), 6.5 and 6.95 (2d, 2, N═C$H_2$), 7.43 (s, 1, (6$H$), 9.2 (br s, 1 N$H$).

EXAMPLE 10
3'-O-(t-Butyldiphenylgilyl)-5'-Deoxy-5'-Iodothymidine 12

To a stirred solution of 3'-O-(t-butyldiphenylsilyl) thymidine [11, 10.0 g, 20.83 mmol, prepared according to the procedure of Koster, et al., *Tet. Letts.* 1982, 26, 2641] in dry DMF (375 ml) was added methyltriphenoxyphosphonium iodide (12.12 g, 30 mmol) under argon at room temperature. The solution was stirred for 16 h. The DMF was removed under reduced pressure and the residue was dissolved in $CH_2Cl_2$ (500 ml). The organic layer was washed with 20% aqueous $Na_2S_2O_3$ (200 ml), water (2×200 ml) and dried ($MgSd_4$). The solvent was evaporated and the residue was purified by silica gel chromatography. Elution with $Et_2O$: Hexanes (1:1, v/v), pooling of appropriate fractions and concentration furnished compound 12 as white power (7.87 g, 64%, mp 142° C.). Anal. Calcd. for $C_{26}H_{31}N_2O_4SiI$: C, 52.88; H, 5.29; N., 4.74; I, 21.33. Found: C,52.86; H, 5.21; N, 4.66; I, 21.54.

EXAMPLE 11
5'-O-(t-Butyldinothylsilyl)-3'-O-Dephouphinico-3'-O-(Imino-methylene)thymidylyl-(3'→5')-3'-O-(t-Butyldiphenylsilyl)-5'-Deoxythymidine, 13

A stirred solution of 5'-O-(t-butyldimethylsilyl)-3'-deoxy-3'-[(methyleneamino)oxy]thymidine (10, 1.62 g, 4.23 mmol), 3'-O-(t-butyldiphenylsilyl)-5'-deoxy-5'-iodothymidine (12, 2.5 g, 4.23 imol), bis(trimethylstannyl)benzopinacolate [4.84 g, 8.46 mmol, prepared according to the method of Hillgartner, et al., *Liebigs Ann. Chem.* 1975, 586] in dry benzene (9 ml) was carefully degassed 3-times (flushed with argon) and heated at 80° C. for 8 h. The reaction mixture was cooled and concentrated under reduced pressure and the residue was purified by silica gel chromatography. The appropriate fractions, which were eluted with $CH_2Cl_2$:MeOH (97:3, v/v), were pooled and concentrated to give dimeric oligonucleoside, compound 13 (1.25 g, 35%) as white foam. $^1H$ NMR ($CDCl_3$) δ 0.09 and 0.13 [2s, 6, (C$H_3)_2$], 0.89 and 1.06 [2s, 9, (C$H_3)_3$], 1.07 and 1.08 [2s, 9, (C$H_3)_3$], 1.87, and 1.90 (2s, 6, 2 C$H_3$), 5.74 (br s, 1, N$H$), 6.20–6.31 (2m, 2, 2 1'$H$), 6.88 (s, 1, C$_6H$), 10.33 and 10.36 (2 br s, 2, 2N$H$) and other protons.

EXAMPLE 12
3'-O-Dephosphinico-3'-O-[(Methylimino)methylene]thysidylyl-(3'→5')-3'-O-(t-Butyldiphenylsilyl)-5'-Deoxythymidine 14

Method A

Compound 13 was treated as per the procedure of Step 3 of Example 8-to simultaneously N-alkylate the imino nitrogen and deblock the 5' silyl blocking group of the 5' nucleoside of the dimer to yield compound 14 as a foam. $^1H$ NMR ($CDCl_3$) δ 1.07 (9, 9, ($CH_3)_3$), 1.85 and 1.88 (2s, 6, 2C$H_3$), 2.56 (8, 3, N—C$H_3$), 4.77 (br s, 1, 5' O$H$), 6.1 and 6.2 (2m, 2, 1'$H$), 7.4 and 7.62 (2m, 10, Ph $H$), 9.05 (br s, 2, 2 N$H$), and other protons.

EXAMPLE 13
3'-O-Dephosphinico-3'-O-[(Methylimino)methylene]thymidylyl-(3'→5')-5'-Deoxythymidine, 15

The 3'-O-(t-butyldiphenylsilyl) blocking group of compound 14 is removed as per the procedure of Step 4 of Example 8 to yield the fully deblocked dimeric oligonucleoside, compound 15.

EXAMPLE 14
3'-O-Dephosphinico-3'-O-[(Methylimino)methylene]-5'-Iodo—5'-Deoxythymidylyl-(3'→5')-3'-O-(t-Butyldiphenylsilyl)-5'-Deoxythysidine, 16

Compound 14 is treated as per the procedure of Example 10 to yield the title dimeric oligonucleoside, compound 16, having a reactive iodo functionality at the terminal 5' position and a blocking group remaining at the 3' position.

EXAMPLE 15
5'-O-(t-Butyldinethylsilyl)-3'-O-Dephosphinico-3'-O-(Imino-methylene)thymidylyl-(3'→5')-3'-O-Dephosphinico-3'-O-[(-Mthyimino)methylene]-5'-Deoxythymidylyl-(3'→5')-3'-O-(t-Butyldiphenylsilyl)-5'-Deoxythymidine, 17

Compound 16 is reacted with compound 10 utilizing the conditions of Example 11 to extend the oligonucleoside to yield the trimeric oligonucleoside, compound 17.

EXAMPLE 16
3'-O-Dephosphinico-3'-O-[(Methylimino)methylene]thymidylyl-(3'→5')-3'-O-Dephosphinico-3'-O-[(Methyimino)methylene]-5'-Deoxythymidylyl-(3'→5')-3'-O-(t-Butyldiphenylsilyl)-5'-Deoxythymidinc, 18

Compound 17 when reacted as per the conditions of Example 12 will undergo N-alkylation to the trimeric oligonucleoside and will be deblock at the 5' position to yield compound 18, wherein n=2.

EXAMPLE 17
3'-O-Dophosphinico-3'-O-[(Methylimino)methylene]thymidylyl-(3'→5')-3'-O-Dephosphinico-3'-O-[(Methyimino)methylene]-5'-Deoxythymidylyl-(3'→5')-3'-O-Dephosphinico-3'-O-[(Methyimino)methylene]-5'-Deozythymidylyl-(3'→5')-5'-Deozythymidine, 20

The sequence of Examples 13, 14, and 15 is repeated for the addition of a further nucleoside to extend the oligonucleoside to a tetramer, compound 19. The tetrameric oligonucleoside 19 is then treated as per the procedure of Example 13 to remove the terminal 3' silyl blocking group yielding the fully deblocked tetrameric oligonucleoside, compound 2.

EXAMPLE 18

5'-O-(t-Butyldimethylsilyl)-2',3'-Dideoxy-3'-[(Methyleneamino)oxy]adenosine, 27; 5'-O-(t-Butyldiaethylsilyl)-2',3'-Dideozy-3'-[(Methylaneamino)oxy]cytidine, 28; and 5'-O-(t-Butyldimethylsilyl)-2',3'-Dideoxy-3'-[(Methyleneamino)oxy]guanosine, 29

3'-O-Amino-2'-deoxyadenosine, compound 24, 3'-O-amino-2'-deoxycytidine, compound 25, and 3'-O-amino-2'-deoxyguanosine, compound 26, prepared as per the procedures of European Patent Application 0 381 335 or in a manner analogous to the preparation of compound 4 by the procedure of Example 7 above, are blocked at their 5' position with a t-butyldimethylsilyl group according to the procedure of Nair, et al., *Org. Prep. Procedures Int.* 1990, 22, 57 to give the corresponding 3'-O-amino-5'-(t-butyldimethylsilyl)-2'-deoxyadenosine, 3'-O-amino-5'-(t-butyldimethylsilyl)-2'-deoxycytidine and 3'-O-amino-5'-(t-butyldimethylsilyl)-2'-deoxyguanosine nucleoside intermediates. Treatment of the blocked intermediate as per the procedure of Example 9 or as per the procedure of Preparation Example 4 of European Patent Application 0 381 335 gives the corresponding 5'-O-(t-butyldimethylsilyl)-2',3'-dideoxy-3'-[(methyleneamino)oxy]adenosine, compound 27; 5'-O-(t-butyldimethylsilyl)-2',3'-dideoxy-3'-[(methyleneamino)oxy]cytidine, compound 28; and 5'-O-(t-butyldimethylsilyl)-2',3'-dideoxy-3'-[(methylene-amino)oxy]guanosine, compound 29.

EXAMPLE 19

Dimer Synthesis

5'-Benzoyl-3'-O-Dephosphinico-3'-O-[(Methylimino)methylene]thymidylyl-(3'→5')-3'-O-(t-Butyldiphenylsilyl)-5'-Deoxythysidine, 35

Compound 34 is reacted with silylated thymine as per the procedure of Baud, et al., *Tetrahedron Letters* 1990, 31, 4437 utilizing dibenzo-18-crown-6 and potassium iodide in acetonitrile-toluene to yield 5'-O-benzoyl-3'-O-dephosphinico-3'-O-[(methylimino)methylene]thymidylyl-(3'→5')-3'-O-(t-butyldiphenylsilyl)-5'-deoxythymidine, compound 35 as an anomeric mixture.

3'-O-Dephosphinico-3'-O-[(Methylimino)methylene]-thymidylyl-(3'→5')-3'-O-(t-Butyldiphenylsilyl)-5'-Deoxyadenosine, 36

Compound 34 is reacted with silylated adenine as per the procedure of Baud, et al., *Tetrahedron Letters* 1990, 31, 4437 utilizing dibenzo-18-crown-6 and potassium iodide in acetonitrile-toluene. Removal of the benzoyl group with methanolic ammonia and chromatographic separation will yield 3'-O-dephosphinico-3'-O-[(methylimino)-methylene]thymidylyl-(3'→5')-3'-O-(t-butyldiphenylsilyl)-5'-deoxyadenosine, 36.

3'-O-Dephosphinico-3'-O-[(Methylimino)methylene-]thymidylyl-(3'→5')-3'-O-(t-Butyldiphenylsilyl)-5'-Deoxycytidine 37

Compound 34 is reacted with silylated cytosine as per the procedure of Baud, et al., *Tetrahedron Letters* 1990, 31, 4437 utilizing dibenzo-18-crown-6 and potassium iodide in acetonitrile-toluene. Removal of the benzoyl group with methanolic ammonia and chromatographic separation will yield 3'-O-dephosphinico-3'-O-[(methylimino)-methylene] thymidylyl-(3'→5')-3'-O-(t-butyldiphenylsilyl)-5'-deoxycytidine, 37.

3'-O-Dephosphinico-3'-O-[(Methylimino)methylene]-thymidylyl-(3'→5')-3'-O-(t-Butyldiphenymlsilyl)-5'-Deoxyguanosin 38

Compound 34 is reacted with silylated guanine as per the procedure of Baud, et al., *Tetrahedron Letters* 1990, 31, 4437 utilizing dibenzo-18-crown-6 and potassium iodide in acetonitrile-toluene. Removal of the benzoyl group with methanolic ammonia and chromatographic separation will yield 3'-O-dephosphinico-3'-O-[(methylimino)-methylene] thymidylyl-(3'→5')-3'-O-(t-butyldiphenylsilyl)-5'-deoxyguanosine, 38.

A-(3'→5')-T; A-(3'→5')-A; A-(3'→5')-C; and A-(3'→5')-G 3'-Dephosphinico-3'-(Methylimino)Methylene Linked Dimers In a manner analogous to the procedures of Examples 19 and 20, the 5'-(t-butyldimethylsilyl)-3'-O-aminoadenosine intermediate of Example 15 will be reacted with compound 3 to yield a linked nucleoside-sugar compound equivalent to compound 34 wherein Bxi is adenine. The linked nucleoside-sugar intermediate will then be reacted as per the procedures of Examples 21, 23, 24 and 25 to yield the A-T, A-A, A-C and A-G diners, respectively, of a structure equivalent to that of compound 14 where Bxi is adenine and Bxj is thymine, adenine, cytosine and guanine, respectively.

C-(3'→5')-T; C-(3'→5')-A; C-(3'→5')-C; and C-(3'→5')-G 3'-Dephosphinico-3'-(Methylimino)methylene Linked Dimers In a manner analogous to the procedures of Examples 19 and 20, the 5'-(t-butyldimethylsilyl)-3'-O-aminocytidine intermediate of Example 15 will be reacted with compound 3 to yield a linked nucleoside-sugar compound equivalent to compound 34 wherein Bxi is cytidine. The linked nucleoside-sugar intermediate will then be reacted as per the procedures of Examples 21, 23, 24 and 25 to yield the C-T, C-A, C-C and C-G dimers, respectively, of a structure equivalent to that of compound 14 where Bxi is cytosine and Bxj is thymine, adenine, cytosine and guanine, respectively.

G-(3'→5')-T; G-(3'→5')-A; G-(3'→5')-C; and G-(3'→5')-G 3'-Dephosphinico-3'-(Methylimino)methylene Linked Dimers In a manner analogous to the procedures of Examples 19 and 20, the 5'-(t-butyldimethylsilyl)-3'-O-aminoguanosine intermediate of Example 15 will be reacted with compound 3 to yield a linked nucleoside-sugar compound equivalent to compound 34 wherein Bxi is guanine. The linked nucleoside-sugar intermediate will then be reacted as per the procedures of Examples 21, 23, 24 and 25 to yield the G-T, G-A, G-C and G-G diners, respectively, of a structure equivalent to that of compound 14 where Bxi is guanine and Bxj is thymine, adenine, cytosine and guanine, respectively.

EXAMPLE 20

Trimeric, Tetraueric, Pentameric, Hexameric And Other Higher Order Oligonucleosides Having a Selected Nucleoside sequence The dimers of Examples 19 are extended by reaction with the 5'-(t-butyldimethylsilyl)-3'-deoxy-3'-[(methyleneamino)oxy] nucleosides, compounds 10, 27, 28 and 29, of Examples 8 and 17 to form trimers utilizing the looping sequence of reactions of Examples 13, 14, and 15. Iteration of this reaction sequence loop adds a further nucleoside to the growing oligonucleoside per each iteration of the reaction sequence loop. The reaction sequence loop of Examples 13, 14, and 15 is repeated "n" number of times to extend the oligonucleoside to the desired "n+1" length. The final 3'-blocked oligonucleoside when treated as per the procedure of Example 13 to remove the terminal 3'-O-(t-butyldiphenylsilyl) blocking group will yield the fully deblocked oligonucleoside of the selected nucleoside sequence and length.

EXAMPLE 21
5'-O-(t-Butyldinethylsilyl)-3'-O-Dephosphinico-3'-O-(Iminomethylene)thymidylyl-(3'→5')-3'-O-(t-Butyldiphenylsilil)-5'-Deoxy-5'-Hydroxythymidine, 48

Utilizing the procedure of Hanamoto, et al., *Tet. Letts.* 1991, 32, 3555, SmI$_2$ (0.1 mmol) in THF (3 ml) is added to a mixture of compound 5 and compound 10 in HMPA (0.5 ml) with stirring. The mixture will be stirred at room temperature for about 15 mins to form the adduct (as detected by the fading color). The solvent will be removed and the residue purified by column chromatography to give the dimeric oligonucleoside 48.

EXAMPLE 22
3'-O-Dephosphinico-3'-O-[N-(Morpholin-2-yl)]thymidylyl-(3'→4')-3'-O-(t-Butyldipheoylsilyl)-5'-Deoxy-5'-Demethylenethymidine, 49

Utilizing the modification of Lim, M.-I. and Pan, Y.-G., *Book of Abstracts*, 203 ACS national Meeting, San Francisco, Calif., Apr. 5–10, 1992, of the procedure of Hill, et al.,*J. Chem. Soc.* 1964, 3709, the dimeric oligonucleoside of Example 21 (compound 48, 1 equiv.) will be treated with chloroacetyl chloride in acetone to form an adduct with the amino group of the linkage. Further treatment with K$_2$CO$_3$ (1.2 equiv.) in DMSO at elevated temperature will cyclize the adduct to the hydroxyl group of the linkage to form a 5-oxomorpholino adduct with the linkage. The oxomorpholino adduct is then reduced with BH$_3$-THF under reflux to yield the dimer linked via an —O—[N-(morpholin-2-yl)]-linkage, compound 49.

EXAMPLE 23
Synthesis Of Oligonucleotides Using A DNA Synthesizer

Solid support oligonucleotide and "oligonucleotide like" syntheses are performed on an Applied Biosystems 380 B or 394 DNA synthesizer following standard phosphoramidite protocols and cycles using reagents supplied by the manufacture. The oligonucleotides are normally synthesized in either a 10 μmol scale or a 3×1 μmol scale in the "Trityl-On" mode. Standard deprotection conditions (30% NH$_4$OH, 55° C., 16 hr) are employed. HPLC is performed on a Waters 600E instrument equipped with a model 991 detector. For analytical chromatography, the following reverse phase HPLC conditions are employed: Hamilton PRP-1 column (15×2.5 cm); solvent A: 50 mm TEAA, pH 7.0; solvent B: 45 mm TEAA with 80% CH$_3$CN; flow rate: 1.5 ml/min; gradient: 5% B for the first 5 minutes, linear (1%) increase in B every minute thereafter. For preparative purposes, the following reverse phase HPLC conditions are employed: Waters Delta Pak Waters Delta-Pak C$_4$ 15 μm, 300A, 25×100 mm column equipped with a guard column of the same material; column flow rate: 5 ml/min; gradient: 5% B for the first 10 minutes, linear 1% increase for every minute thereafter. Following HPLC purification, oligonucleotides are detritylated and further purified by size exclusion using a Sephadex G-25 column.

EXAMPLE 24
Higher Order Mixed Oligonucleosides-oligonucleosides And Mixed oligonucleosides-oligonucleotides A. Solution Phase Synthesis Of 3'-De(oxophosphinico)-3'-[Methyl(iminooxymethylone)]-Thymidylyl-(3'→5')-5'-Deoxythymidylyl-3'-Phosphorothioate-Thymidylyl-(3'→5')-3'-De(oxyphosphinico)-3'-[(Methylimino)-1,2-Ethanediyl]thymidylyl-(3'→5')-3'-O-(t-Butyldiphenylsilyl)-5'-Deoxythymidine, 90, A Mixed oligonucleoside-oligonualeotide-oligonucleoside Polymer Incorporating A Nucleotide Linkage Flanked At Its 5' Terminus By A 3'-De(oxophosphinico)-3'-[Methyl(iminoozymethylene)] Linked Oligonucleoside Dimer and At Its 3' Terminus By A 3'-De(oxyphosphinico)-3'-[(Methylimino)-1,2-Ethanediyl] Linked oligonucleoside Dimer A mixed oligonucleoside-oligonucleotide-oligonucleotside having a 3'-de(oxophosphinico)-3'-[methyl (iminooxymethylene)]linked oligonucleoside dimer and a 3'-de(oxyphosphinico)-3"-[(methylimino)-1,2-ethanediyl] linked oligonucleoside dimer coupled together via a phosphorothioate nucleotide linkage will be prepared by reacting compoundy 58, compound 70 and tetrazole in anhydrous acetonitrile under argon. The coupling reaction will be allowed to proceed to completion followed by treatment with Beaucage reagent and ammonium hydroxide removal of the dimethoxytrityl blocking group according to the procedure of Zon, G. and Stec, W. J., *Phosphorothioate oligonucleotides, oligonucleotides and Analogs A Practical Approach*, F. Eckstein Ed., IRL Press, pg. 87 (1991). The 3' blocking group will then removed as per the procedure of Step 3 of Example 8 and the product purified by HPLC to yield the title compound 90, wherein utilizing the structure of Scheme XI, T$_3$ and T$_5$ are OH, D is S, E is OH, X is H, Q is O, r is O and q is 2; and for each q, i.e. q$_1$ and q$_2$, n and p are 1 in each instance; and for q$_1$, m is 1; and for q$_2$, m is 0; and Bxj and Bxi are thymine.

B. Solid Support Synthesis Of 3'-De(oxophosphinico)-3"-[Methyl(iminoozymethylone)]-Thymidylyl-(3'→5')-5'-Deoxythymidylyl-(3'→5')-P-Thylidylyl-3'-De(oxophosphinico)-3'-[Methyl(iminooxymethylone)]-(3'→5')-Thymidylyl-(3'→5')-P-Thylidylyl-3'-De(oxophosphinico)-3'-[Methyl(iminooxymethylene)]-(3'→5')-Thymidylyl-(3'→5')-P-2'-Deoxycytidine, 91, A Mized Oligonucleotide-Oligonuclooside Polymer incorporating 3'-De(oxophos-phinico)-3'-[Methyl (iminooxymthylemn)] Linked Oligonucleoside Dimers Planked By Conventional Linked Nuclcotides The dimeric oligonucleoside 58 will be utilized as building block units in a conventional oligonucleotide solid support synthesis as per the procedure of Example 23. For the purpose of illustration a polymer incorporating seven nucleosides is described. A first unit of the dimeric oligonucleoside 58 will be coupled to a first cytidine nucleoside tethered to a solid support via its 3' hydroxyl group and having a free 5' hydroxyl group. After attachment of the first unit of compound 58 to the support, the 5'-dimethoxytrityl group of that first compound 58 unit will be removed in the normal manner. A second compound 58 unit will then be coupled via its β-cyanoethyl-N-diisopropylphosphiryl group to the first compound 58 unit using normal phosphoramidate chemistry. This forms a conventional phosphodiester bond between the first and second compound 58 units and elongates the polymer by two nucleosides (or one oligonucleoside dimer unit). The dimethoxytrityl blocking group from the second compound 58 unit will be removed in the normal manner and the polymer elongated by a further dimeric unit of compound 58. As with addition of the first and second dimeric units, the third unit of compound 58 is coupled to the second via conventional phosphoramidite procedures. The addition of the third unit of compound n completes the desired length and base sequence. This polymer has a backbone of alternating normal phosphodiester linkages and the methyl-(iminooxymethylene) linkages of compound 58. The 5' terminal dimethoxytrityl group of the third compound 58 unit will be removed in the normal manner followed by release of the polymer from the solid support, also in the normal manner. Purification of the polymer will be achieved by HPLC to yield compound 91 wherein, utilizing the structure of Scheme XI, $T_3$ and $T_5$ are OH, D is O, E is OH, X is H, Q is O, r is 1 and for the seven nucleoside polymer described, q is 3; and for each q, i.e. $q_1$, $q_2$ and $q_3$, n and p are 1 in each instances; and for $q_1$ and $q_2$, m is 1; and for $q_3$, n is 0; and Bxk is cytosine; and each BxJ and Bxi is thymine.

EXAMPLE 25
General method for 3'-deoxy-3'-iodo nucleosides

The preparation of 3'-deoxy-3'-iodo-5'-O-tritylthymidine has been described by Verhyden, et al., *J. Org. Chem.* 1970, 35, 2868. In an analogous manner, 2',3'-dideoxy- 3'-iodo-5'-O-trityluridine, cytidine, adenosine and guanosine will be prepared.

EXAMPLE 26
Synthesis of Bifunctional Nucleosides

5"-Deoxy-5'iodo-3'-O-phthalisidothysidine, 102

Treatment of 3'-O-phthalimidothymidine with methyltriphenoxyphosphonium iodide (Example 10) furnished 48% of 102; m.p. 145–146° C.; Anal. Calcd. for $C_{18}H_{16}N_3O_6I$: C, 43.48; H, 3.24; N, 8.48; I, 25.52. Found: C, 43.75; H, 3.34; N, 8.38; I, 25.59. $^1H$ NMR (CDCl$_3$) δ 8.01 (s, 3, $C_5CH_3$), 2.58–2.67 (m, 2, 2'CH$_2$), 3.54–3.78 (m, 2, 5' CH$_2$), 4.30–4.34 (m, 1, 4'H), 5.01–5.03 (m, 1, 3'H), 6.38 (dd, 1, 1'H), 7.77–7.78 (m, 6, $C_5H$ and ArH), 8.69 (br s, 1, NH).

3'-deozy-3'-iodo-5'-O-phthalimidothymidine, 109

Treatment of 5'-O-phthalimidothymidine (Example 1) with methyltriphenoxyphosphoniuniodide in an analogous manner gave 43% of 1; m.p. 130 (decomposes); Anal. Calcd. for $C_{18}H_{16}N_3O_6I$:C, 43.75; H, 3.24; N, 8.45; I, 25.52. Found: C, 54.82, H, 3.24; N, 8.45; I, 25.18. $^1H$ NMR (CDCl$_3$) δ 1.94 (s, 3, C5CH$_3$), 2.70–2.79 (m, 2, 2'CH$_2$), 4.53–4.56 (m, 3, 5'CH$_2$, 3'H), 4.67 (m, 1, 4'H), 6.28 (5, 1, 1'H), 7.70 (5, 1, CH$_6$H), 7.71–7.90 (m, 4, ArH), 8.55 (br s, 1, NH).

EXAMPLE 27
Incorporation Of Phosphodiester Linkages

Dimeric nucleosides 117c (R'=ODMTr, R"=O-amidite) and 119b (R'=ODMTr, R"=O-amidite), and trimeric nucleoside 118d (R'=ODMTr, R"=O-amidite, $L_2=L_{2a}=N-CH_3$) were prepared generally in accordance with Sproat, et al., Oligonucleotides and Analogs A Practical Approach, Eckstein, ed., IRL Press, 1991.

3'-De(oxyphosphinico)-3'-O-(iminomethylene)-5'-dimethyoxytritylthymidylyl-(3'→5')-3"-[(β-cyanoethyoxy)-N-(diisopropyl)phosphiryl]-5'-deoxythymidine 117c was obtained as a white foam (mixture of diastereoisomer): $^{31}P$ NMR (CD$_3$CN) δ 149.1 and 149.5 ppm; $^1H$ NMR (CD$_3$CN) δ 1.6 and 1.75 (2S, 6 2C$_5$CH$_3$), 2.20 (S, 3, N—CH$_3$), 6.1 (m, 2, 1'H), 9.0 (br S, 2, NH) and other protons.

3'-De(oxyphosphinico)-3'-[(methylene(methylimino)]-thymidyl-5'-O-(dimethytrityl)-(3'→5')-3'-O-(β-cyanoethyl diisopropylaminophosphilyl)thymidine 118d was obtained as white proipitate (mixture of diastereoisomer): 31P NMR (CDCl$_3$) δ 149.62 and 149.11 ppm; $^1H$ NMR (CDCl$_3$) δ 1.82 and 1.49 (2S, 6, 2C$_5$CH$_3$), 2.58 and 2.56 (2S, 3, N—CH$_3$), 6.16 (pseudo t, 1, T1-1'H, $J_{=1',2"}=J_{1',2"}=5.8$ Hz), 6.22 (pseudo t, 1, T2 1'H, $J_{=1',2"}=J_{1',2"}=6.7$ Hz), and other protons.

Phosphoramidites 117c, 118d, and 119b can be stored and used for coupling by automated DNA synthesizer (e.g., ABI 380 B) as and when required for specific incorporation into oligomers of therapeutic value. Other dimers of the inventions can be incorporated into oligomers in a similar manner. This permits flexibility in converting oligonucleosides prepared via radical coupling methodology of this invention into standard phosphoramidites, which can be utilized as "blocks of synthetic DNA" to improve the pharmacokinetic and pharmacodynamic properties of antisense oligomers.

EXAMPLE 28
Enzymatic Degradation

5'GCGTTTTT*TTTTTGCG3' (*=3'—CH$_2$—N(CH$_3$)—O—CH$_2$—4' linkage; 30 nanomoles) was dissolved in 20 ml of buffer containing 50 mM Tris-HCl pH 8.5, 14 mM MgCl$_2$, and 72 mM NaCl. To this solution 0.1 units of snake-venom phosphodiesterase (Pharmacia, Piscataway, N.J.), 23 units of nuclease P1 (Gibco LBRL, Gaithersberg, Md.), and 24 units of calf intestinal phosphatase (Boehringer Mannheim, Indianapolis, Ind.) was added and the reaction mixture was incubated at 37° C. for 100 h. HPLC analysis was carried out using a Waters model 715 automatic injector, model 600E pump, model 991 detector, and an Alltech (Alltech Associates, Inc., Deerfield, Ill.) nucleoside/nucleotide column (4.6×250 mm). All analyses were performed at room temperature. The solvents used were A: water and B: acetonitrile. Analysis of the nucleoside composition was accomplished with the following gradient: 0–5 min., 2% B (isocratic); 5–20 min., 2% B to 10% B (linear); 20–40 min., 10% B to 50% B. The integrated area per nanomole was determined using nucleoside standards. The T*T diner containing the N-methylaminohydroxy linkage was quantitated by evaluation as if it were a thymidine nucleoside. Relative nucleoside ratios were calculated by converting integrated areas to molar values and comparing all values to thymidine, which was set at its expected value for each oligomer.

EVALUATION

PROCEDURE 1-Nuclease Resistance

A. Evaluation of the resistance of oligonucleotide-mimickinq macromolecules to serum and cytoplasmic nucleases.

Oligonucleotide-mimicking macromolecules of the invention can be assessed for their resistance to serum nucleases by incubation of the oligonucleotide-mimicking macromolecules in media containing various concentrations of fetal calf serum or adult human serum. Labeled oligonucleotide-mimicking macromolecules are incubated for various times, treated with protease K and then analyzed by gel electrophoresis on 20% polyacrylamine-urea denaturing gels and subsequent autoradiography. Autoradiograms are quantitated by laser densitometry. Based upon the location of the modified linkage and the known length of the oligonucleotide-mimicking macromolecules it is possible to determine the effect on nuclease degradation by the particular modification. For the cytoplasmic nucleases, an HL 60 cell line can be used. A post-mitochondrial supernatant is prepared by differential centrifugation and the labelled macromolecules are incubated in this supernatant for various times. Following the incubation, macromolecules are assessed for degradation as outlined above for serum nucleolytic degradation. Autoradiography results are quantitated for evaluation of the macromolecules of the invention. It is expected that the macromolecules will be completely resistant to serum and cytoplasmic nucleases.

B. Evaluation of the resistance of oligonucleotide-simicking macromolecules to specific endo- and ezonucleases.

Evaluation of the resistance of natural oligonucleotides and oligonucleotide-mimicking macromolecules of the invention to specific nucleases (ie, endonucleases, 3',5'-exo-, and 5',3'-exonucleases) can be done to determine the exact effect of the macromolecule linkage on degradation. The oligonucleotide-mimicking macromolecules are incubated in defined reaction buffers specific for various selected nucleases. Following treatment of the products with protease K, urea is added and analysis on 20% polyacrylamide gels containing urea is done. Gel products are visualized by staining with Stains All reagent (Sigma Chemical Co.). Laser densitometry is used to quantitate the extent of degradation. The effects of the macromolecules linkage are determined for specific nucleases and compared with the results obtained from the serum and cytoplasmic systems. As with the serum and cytoplasmic nucleases, it is expected that the oligonucleotide-mimicking macromolecules of the invention will be completely resistant to endo- and exo-nucleases.

C. Nuclease Degradation studies

It has been reported that terminal phosphorothioate and methylphosphonate modifications stabilize an oligonucleotide to 3' and 5' exonucleases such as snake venom phosphodiesteraser, spleen phosphodiesterase, calf serum, and cell media (see, e.g., Nucleic Acids Res. 1991, 19, 747 and 5473). The novel backbones of this invention confer similar or sometimes better protection from enzymatic exonucleolytic degradation. The inventors recently reported (J. Am. Chem. Soc. 1992, 114, 4006) that incorporation of a single 3'-CH$_2$—N(CH$_3$)—O—CH2—4' backbone at the 3' terminus of an oligomer enhanced the half-life of modified oligomer compared to the natural unmodified oligomer. These oligonucleosides exhibited a significant resistance to nucleases while maintaining a high level of base pair specificity. Therefore, the following oligonucleosides were modified at their terminal positions (3' and/or 5') with 3'—CH$_2$—N(CH$_3$)—O—CH2—4' linkages to block exonucleolytic degradation.

| No. | Oligonucleoside Sequence | T ½ (Hours) |
| --- | --- | --- |
| 1 | TTTTTTTTTC | 0.2 |
| 2 | T*TT*TTTT*TT*TC | 0.4 (11 mer) 11 (10-mer) |
| 3 | T*TTTTTTT*TC | 0.4 (11-mer) 6 (10-mer) |
| 4 | T*TT*TT*TT*TT*TC | 0.4 (11-mer) 16 (10-mer) |
| 5 | T*T*T*T | No degradatian! (up to ~ 60 hours) |

Results for Entries 1–4, above, correspond to SEQ ID NO: 1 Entries 2–4 showed a characteristic 3'-exonuclease-dominant degradation pattern characterized by rapid cleavage of 3'-C residue from all oligomers. Aside from the 3'-phosphodiester linkages, the 10-mers appear to be significantly resistant towards degradation compared to the unmodified oligomer (Entry 1). The fully modified tetramer (Entry 5), which contains no phosphodiester linkage, showed complete stability up to 60 hours of incubation in cell extract (see, Nucleic Acids Res. 1991, 19, 5743 for experimental details). Since the phosphodiester linkage is the site of nucleolytic attack, complete stability for the fully modified oligomer was expected. These results taken together suggests that an end-capped (3' and 5') oligomer containing achiral and neutral backbone will have enhance half-life.

PROCEDURE 2-5-Lipoxygenase Analysis and Assays

A. Therapeutics

For therapeutic use, an animal suspected of having a disease characterized by excessive or abnormal supply of 5-lipoxygenase is treated by administering the macromolecule of the invention. Persons of ordinary skill can easily determine optimum dosages, dosing methodologies and repetition rates. Such treatment is generally continued until either a cure is effected or a diminution in the diseased state is achieved. Long term treatment is likely for some diseases.

B. Research Reagents

The oligonucleotide-mimicking macromolecules of this invention will also be useful as research reagents when used to cleave or otherwise modulate 5-lipoxygenase mRNA in crude cell lysates or in partially purified or wholly purified RNA preparations. This application of the invention is accomplished, for example, by lysing cells by standard methods, optimally extracting the RNA and then treating it with a composition at concentrations ranging, for instance, from about 100 to about 500 ng per 10 Mg of total RNA in a buffer consisting, for example, of 50 mm phosphate, pH ranging from about 4–10 at a temperature from about 300 to about 50° C. The cleaved 5-lipoxygenase RNA can be analyzed by agarose gel electrophoresis and hybridization with radiolabeled DNA probes or by other standard methods.

C. Diagnostics

The oligonucleotide-mimicking macromolecules of the invention will also be useful in diagnostic applications, particularly for the determination of the expression of specific mRNA species in various tissues or the expression of abnormal or mutant RNA species. In this example, while the macromolecules target a abnormal mRNA by being designed complementary to the abnormal sequence, they would not hybridize to normal mRNA.

Tissue samples can be homogenized, and RNA extracted by standard methods. The crude homogenate or extract can be treated for example to effect cleavage of the target RNA. The product can then be hybridized to a solid support which contains a bound oligonucleotide complementary to a region on the 5' side of the cleavage site. Both the normal and abnormal 5' region of the mRNA would bind to the solid support. The 3' region of the abnormal RNA, which is cleaved, would not be bound to the support and therefore would be separated from the normal mRNA.

Targeted mRNA species for modulation relates to 5-lipoxygenase; however, persons of ordinary skill in the art will appreciate that the present invention is not so limited and it is generally applicable. The inhibition or modulation of production of the enzyme 5-lipoxygenase is expected to have significant therapeutic benefits in the treatment of disease. In order to assess the effectiveness of the compositions, an assay or series of assays is required.

D. In Vitro Assays

The cellular assays for 5-lipoxygenase preferably use the human promyelocytic leukemia cell line HL-60. These cells can be induced to differentiate into either a monocyte like cell or neutrophil like cell by various known agents. Treatment of the cells with 1.3% dimethyl sulfoxide, DMSO, is known to promote differentiation of the cells into neutrophils. It has now been found that basal HL-60 cells do not synthesize detectable levels of 5-lipoxygenase protein or secrete leukotrienes (a downstream product of 5-lipoxygenase). Differentiation of the cells with DMSO causes an appearance of 5-lipoxygenase protein and leukotriene biosynthesis 48 hours after addition of DMSO. Thus induction of 5-lipoxygenase protein synthesis can be utilized as a test system for analysis of oligonucleotide-mimicking macromolecules which interfere with 5-lipoxygenase synthesis in these cells.

A second test system for oligonucleotide-mimicking macromolecules makes use of the fact that 5-lipoxygenase is a "suicide" enzyme in that it inactivates itself upon reacting with substrate. Treatment of differentiated HL-60 or other cells expressing 5 lipoxygenase, with 10 $\mu$M A23187, a calcium ionophore, promotes translocation of 5-lipoxygenase from the cytosol to the membrane with subsequent activation of the enzyme. Following activation and several rounds of catalysis, the enzyme becomes catalytically inactive. Thus, treatment of the cells with calcium ionophore inactivates endogenous 5-lipoxygenase. It takes the cells approximately 24 hours to recover from A23187 treatment as measured by their ability to synthesize leukotriene B. Macromolecules directed against 5-lipoxygenase can be tested for activity in two HL-60 model systems using the following quantitative assays. The assays are described from the most direct measurement of inhibition of 5-lipoxygenase protein synthesis in intact cells to more downstream events such as measurement of 5-lipoxygenase activity in intact cells.

A direct effect which oligonucleotide-mimicking macromolecules can exert on intact cells and which can be easily be quantitated is specific inhibition of 5-lipoxy-genase protein synthesis. To perform this technique, cells can be labelled with $^{35}$S-methionine (50 $\mu$Ci/mL) for 2 hours at 37° C. to label newly synthesized protein. Cells are extracted to solubilize total cellular proteins and 5-lipoxygenase is immunoprecipitated with 5-lipoxygenase antibody followed by elution from protein A Sepharose beads. The immunoprecipitated proteins are resolved by SDS-polyacrylamide gel electrophoresis and exposed for autoradiography. The amount of immunoprecipitated 5-lipoxygenase is quantitated by scanning densitometry.

A predicted result from these experiments would be as follows. The amount of 5-lipoxygenase protein immunoprecipitated from control cells would be normalized to 100%. Treatment of the cells with 1 $\mu$M, 10 $\mu$M, and 30 $\mu$M of the macromolecules of the invention for 48 hours would reduce immunoprecipitated 5-lipoxygenase by 5%, 25% and 75% of control, respectively.

Measurement of 5-lipoxygenase enzyme activity in cellular homogenates could also be used to quantitate the amount of enzyme present which is capable of synthesizing leukotrienes. A radiometric assay has now been developed for guantitating 5-lipoxygenase enzyme activity in cell homogenates using reverse phase HPLC. Cells are broken by sonication in a buffer containing protease inhibitors and EDTA. The cell homogenate is centrifuged at 10,000×g for 30 min and the supernatants analyzed for 5-lipoxygenase activity. Cytosolic proteins are incubated with 10 $\mu$M $^{14}$C-arachidonic acid, 2 mM ATP, 50 $\mu$M free calcium, 100 $\mu$g/ml phosphatidylcholine, and 50 mM bis-Tris buffer, pH 7.0, for 5 min at 37° C. The reactions are quenched by the addition of an equal volume of acetone and the fatty acids extracted with ethyl acetate. The substrate and reaction products are separated by reverse phase HPLC on a Novapak C18 column (Waters Inc., Millford, Mass.). Radioactive peaks are detected by a Beckman model 171 radiochromatography detector. The amount of arachidonic acid converted into di-HETE's and mono-HETE's is used as a measure of 5-lipoxygenase activity.

A predicted result for treatment of DMSO differentiated HL-60 cells for 72 hours with effective the macromolecules of the invention at 1 $\mu$M, 10 $\mu$M, and 30 $\mu$M would be as follows. Control cells oxidize 200 pmol arachidonic acid/5 min/106 cells. Cells treated with 1 $\mu$M, 10 $\mu$M, and 30 $\mu$M of an effective oligonucleotide-mimicking macromolecule would oxidize 195 pmol, 140 pmol, and 60 pmol of arachidonic acid/5 min/$10^6$ cells respectively.

A quantitative competitive enzyme linked immunosorbant assay (ELISA) for the measurement of total 5-lipoxygenase protein in cells has been developed. Human 5-lipoxygenase expressed in E. coli and purified by extraction, Q-Sepharose, hydroxyapatite, and reverse phase HPLC is used as a standard and as the primary antigen to coat microtiter plates. 25 ng of purified 5-lipoxygenase is bound to the microtiter plates overnight at 4° C. The wells are blocked for 90 min with 5% goat serum diluted in 20 mM Tris●HCL buffer, pH 7.4, in the presence of 150 mM NaCl (TBS). Cell extracts (0.2% Triton X-100, 12,000×g for 30 min.) or purified 5-lipoxygenase were incubated with a 1:4000 dilution of 5-lipoxygenase polyclonal antibody in a total volume of 100 $\mu$L in the microtiter wells for 90 min. The antibodies are prepared by immunizing rabbits with purified human recombinant 5-lipoxygenase. The wells are washed with TBS containing 0.05% tween 20 (TBST), then incubated with 100 $\mu$L of a 1:1000 dilution of peroxidase conjugated goat anti-rabbit IgG (Cappel Laboratories, Malvern, Pa.) for 60 min at 25° C. The wells are washed with TBST and the amount of peroxidase labelled second antibody determined by development with tetramethylbenzidine.

Predicted results from such an assay using a 30 mer oligonucleotide-mimicking macromolecule at 1 $\mu$M, 10 $\mu$M, and 30 $\mu$M would be 30 ng, 18 ng and 5 ng of 5-lipoxygenase per $10^6$ cells, respectively with untreated cells containing about 34 ng 5-lipoxygenase.

A net effect of inhibition of 5-lipoxygenase biosynthesis is a diminution in the quantities of leukotrienes released from stimulated cells. DMSO-differentiated HL-60 cells release leukotriene B4 upon stimulation with the calcium ionophore A23187. Leukotriene B4 released into the cell medium can be quantitated by radioimmunoassay using commercially available diagnostic kits (New England Nuclear, Boston, Mass.). Leukotriene B4 production can be detected in HL-60 cells 48 hours following addition of DMSO to differentiate the cells into a neutrophil-like cell. Cells ($2\times10^5$ cells/mL) will be treated with increasing concentrations of the macromolecule for 48–72 hours in the presence of 1.3% DMSO. The cells are washed and resuspended at a concentration of $2\times10^6$ cell/mL in Dulbecco's phosphate buffered saline containing 1% delipidated bovine serum albumin. Cells are stimulated with 10 $\mu$M calcium ionophore A23187 for 15 min and the quantity of LTB4 produced from $5\times10^5$ cell determined by radioimmunoassay as described by the manufacturer.

Using this assay the following results would likely be obtained with an oligonucleotide-mimicking macromolecule directed to the 5-LO mRNA. Cells will be treated for 72 hours with either 1 $\mu$M, 10 $\mu$M or 30 $\mu$M of the macromolecule in the presence of 1.3% DMSO. The quantity of $LTB_4$ produced from 5×10 cells would be expected to be about 75 pg, 50 pg, and 35 pg, respectively with untreated differentiated cells producing 75 pg $LTB_4$.

E. In Vivo Assay

Inhibition of the production of 5-lipoxygenase in the mouse can be demonstrated in accordance with the following protocol. Topical application of arachidonic acid results in the rapid production of leukotriene $B_4$, leukotriene $C_4$ and prostaglandin $E_2$ in the skin followed by edema and cellular infiltration. Certain inhibitors of 5-lipoxygenase have been known to exhibit activity in this assay. For the assay, 2 mg of arachidonic acid is applied to a mouse ear with the contralateral ear serving as a control. The polymorphonuclear cell infiltrate is assayed by myeloperoxidase activity in homogenates taken from a biopsy 1 hour following the administration of arachidonic acid. The edematous response is quantitated by measurement of ear thickness and wet weight of a punch biopsy. Measurement of leukotriene $B_4$ produced in biopsy specimens is performed as a direct measurement of 5-lipoxygenase activity in the tissue. Oigonucleotide-mimicking macro-molecules will be applied topically to both ears 12 to 24 hours prior to administration of arachidonic acid to allow optimal activity of the compounds. Both ears are pre-treated for 24 hours with either 0.1 μmol, 0.3 μmol, or 1.0 μmol of the macromolecule prior to challenge with arachidonic acid. Values are expressed as the mean for three animals per concentration. Inhibition of polymorphonuclear cell infiltration for 0.1 μmol, 0.3 μmol, and 1 μmol is expected to be about 10%, 75% and 92% of control activity, respectively. Inhibition of edema is expected to be about 3%, 58% and 90%, respectively while inhibition of leukotriene $B_4$ production would be expected to be about 15%, 79% and 99%, respectively.

Those skilled in the art will appreciate that numerous changes and modifications can be made to the preferred embodiments of the invention and that such changes and modifications can be made without departing from the spirit of the invention. It is therefore intended that the appended claims cover all such-equivalent variations as fall within the true spirit and scope of the invention.

$Y_1$ is H, hydroxymethyl, a nucleoside, a nucleotide, an oligonucleotide, an oligonucleoside, or a hydroxyl-protected or amine-protected derivative thereof;

$B_{X1}$ is a nucleosidic base;

$Q_1$ is O, S, $CH_2$, CHF or $CF_2$; and $X_1$ is H, OH, $C_1$ to $C_{10}$ lower alkyl, substituted lower alkyl, alkaryl or aralkyl, F, Cl, Br, CN, $CF_3$, $OCF_3$, OCN, O-alkyl, S-alkyl, N-alkyl, O-alkenyl, S-alkenyl, N-alkenyl, $SOCH_3$, $SO_2CH_3$, $ONO_2$, $NO_2$, $N_3$, $NH_2$, heterocycloalkyl, heterocycloalkaryl, aminoalkylamino, polyalkylamino or substituted silyl.

2. The compound of claim 1 wherein $R_A$ is O.

3. The compound of claim 1 wherein $R_A$ is NH.

4. The compound of claim 1 wherein $Z_1$ is $CH_2$—$R_S$ or $R_S$.

5. The compound of claim 1 wherein $Z_1$ is $R_A$—N=$CH_2$ or $CH_2$—$R_a$-N=$CH_2$.

6. The compound of claim 1 wherein said radical generating group is I.

---

---

What is claimed:

1. A compound having structure:

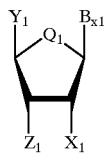

wherein:

$Z_1$ is $CH_2$—$R_B$, $R_B$, $CH_2$—$R_A$N=$CH_2$, or $R_A$N=$CH_2$, provided that $Z_1$ is not $R_A$N=$CH_2$ when $X_1$ is H or OH, and $Z_1$ is not $R_B$ when $R_B$ is OC(O)O—$C_6H_5$;

$R_A$ is O or NH;

$R_B$ is a radical generating group selected from I, OC(O)O—$C_6H_5$, OC(O)S—$C_6H_5$, Se—$C_6H_5$, O—C(S)O—$C_6F_5$, O—C(S)O—$C_6Cl_5$, O—C(S)O—(2,4,6—$C_6Cl_3$), $NO_2$, C(S)S—Me, C(S)O—(p—$CH_4F$), bis-dimethylglyoximato-pyridine cobalt, O—C(S)$C_6H_5$, O—C(S)$SCH_3$, O—C(S)-imidazole, and C(O)O-pyridin-2-thione;

7. A compound having structure:

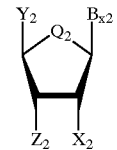

wherein:

$Y_2$ is $CH_2$—$R_B$, $R_B$, $CH_2$—$R_A$N=$CH_2$, or $R_A$N=$CH_2$;

$R_A$ is O or NH;

$R_B$ is a radical generating group selected from I, OC(O)O—$C_6H_5$, OC(O)S—$C_6H_5$, Se—$C_6H_5$, O—(S)O—$C_6F_5$, O—(S)O—$C_6Cl_5$, O—(S)O—(2,4,6—$C_6Cl_3$), Br, $NO_2$, Cl, C(S)S—Me, C(S)O—(p—$CH_4F$), bis-dimethylglyoximato-pyridine cobalt, O(S)$C_6H_5$, O(S)$SCH_3$, O(S)-imidazole, and C(O)O-pyridin-2-thione;

$Z_2$ is H, hydroxyl, a nucleoside, a nucleotide, an oligonucleotide, an oligonucleoside, or a hydroxyl-protected or amine-protected derivative thereof;

$B_{X2}$ is a nucleosidic base;

$Q_2$ is O, S, $CH_2$, CHF or $CF_2$; and $X_2$ is H, OH, $C_1$ to $C_{10}$ lower alkyl, substituted lower alkyl, alkaryl or aralkyl, F, Cl, Br, CN, $CF_3$, $OCF_3$, OCN, O-alkyl, S-alkyl, N-alkyl, O-alkenyl, S-alkenyl, N-alkenyl, $SOCH_3$, $SO_2CH_3$, $ONO_2$, $NO_2$, $N_3$, $NH_2$, heterocycloalkyl, heterocycloalkaryl, aminoalkylamino, polyalkylamino or substituted silyl;

provided that $R_B$ is not I, Br, or Cl when $Z_2$ is hydroxyl, $Q_2$ is O, and $X_2$ is H or OH.

8. The compound of claim 7 wherein $R_A$ is O.

9. The compound of claim 7 wherein $R_A$ is NH.

10. The compound of claim 7 wherein $Y_2$ is $CH_2$—$R_S$ or $R_S$.

11. The compound of claim 7 wherein $Y_2$ is $CH_2$—$R_A$—$N$=$CH_2$ or $R_A$—$N$=$CH_2$.

12. The compound of claim 7 wherein said radical generating group is I.

* * * * *